United States Patent [19]

Nakamura et al.

[11] Patent Number: 5,622,810

[45] Date of Patent: Apr. 22, 1997

[54] SILVER HALIDE COLOR PHOTOSENSITIVE MATERIAL

[75] Inventors: Takashi Nakamura; Hiroshi Fukuzawa; Michio Ono, all of Minami-Ashigara, Japan

[73] Assignee: Fuji Photo Film Co., Ltd., Kanagawa, Japan

[21] Appl. No.: 544,935

[22] Filed: Oct. 18, 1995

[30] Foreign Application Priority Data

| Oct. 18, 1994 | [JP] | Japan | 6-252420 |
| Jan. 20, 1995 | [JP] | Japan | 7-007343 |
| Jan. 23, 1995 | [JP] | Japan | 7-008093 |

[51] Int. Cl.$^6$ .................................................. G03C 1/06
[52] U.S. Cl. .......................... 430/264; 430/598; 430/601; 430/551
[58] Field of Search ...................... 430/264, 551, 430/598, 601

[56] References Cited

U.S. PATENT DOCUMENTS

| 4,681,836 | 7/1987 | Inoue et al. | 430/264 |
| 4,999,275 | 3/1991 | Kasama et al. | 430/264 |
| 5,175,074 | 12/1992 | Yagihara et al. | 430/598 |

FOREIGN PATENT DOCUMENTS

| 0338785 | 10/1989 | European Pat. Off. |
| 60-140340 | 7/1985 | Japan. |
| 3-164735 | 7/1991 | Japan. |

*Primary Examiner*—Geraldine Letscher
*Attorney, Agent, or Firm*—Birch, Stewart, Kolasch & Birch, LLP

[57] ABSTRACT

A silver halide color photosensitive material is disclosed, which has on a support at least one photosensitive silver halide emulsion layer, wherein at least one nondiffusible compound represented by the following formula (I) is contained to inhibit generation of color stain and color fog and to ensure excellent keeping quality:

$$R^1-\underset{H}{N}-\underset{H}{N}-\underset{OR^3}{\overset{\overset{X}{\|}}{P}}-R^2 \quad (I)$$

wherein $R^1$ represents an aryl group or a heterocyclic group, $R^2$ represents an alkyl group, a cycloalkyl group, an alkoxy group or an aryloxy group, $R^3$ represents an alkyl group, a cycloalkyl group, an aryl group or a heterocyclic group and X represents an oxygen atom or a sulfur atom; provided that $R^3$ does not represent a phenyl group when $R^2$ represents a phenoxy group.

$$R^1-\underset{|}{\overset{A^1}{N}}-\underset{|}{\overset{A^2}{N}}-\overset{\overset{X}{\|}}{P}\diagdown_{Y^1} \quad (I\text{-}1)$$

wherein $R'^1$ represents an aryl group or a heterocyclic group; $A'^1$ and $A'^2$ each represents a hydrogen atom or a hydrolyzable group; X represents an oxygen atom or a sulfur atom; and $Y^1$ represents atoms completing a phosphorus-containing heterocyclic ring.

$$(R'^1-\underset{|}{\overset{A^1}{N}}-\underset{|}{\overset{A^2}{N}}\!\!)_m-\overset{\overset{X}{\|}}{G}\!\!-\!\!(R''^2)_n \quad (I\text{-}2)$$

wherein $R''^1$ represents an aryl group or a heterocyclic group; $R''^2$ represents an alkyl group, a cycloalkyl group, an aryl group, a heterocyclic group, an alkoxy group or an aryloxy group; $A''^1$ and $A''^2$ each represent a hydrogen atom or a hydrolyzable group; G represents a carbon atom or a phosphorus atom; X represents an oxygen atom or a sulfur atom; when G represents a carbon atom, m is 2 and n is 0; when G represents a phosphorus atom, m is 2 and n is 1, or m is 3 and n is 0; and two or three $R''^1N(A''^1)N(A''^2)$— groups may be the same or different. A compound represented by the formula (I-1) or (II-1) is also disclosed.

22 Claims, No Drawings

SILVER HALIDE COLOR PHOTOSENSITIVE MATERIAL

FIELD OF THE INVENTION

The present invention relates to a silver halide color photosensitive material and, more particularly, to a sensitive material which contains a hydrazine compound to reduce color stain and color fog and to excert an improved storage stability.

BACKGROUND OF THE INVENTION

A silver halide color photosensitive material has so far been well-known to generate undesirable color stain between silver halide emulsion layers different in color sensitivity. As a means to inhibit the color stain, there is proposed, e.g., the method of using hydroquinone compounds in U.S. Pat. No. 4,732,845. Although hydroquinone compounds have some effect upon inhibition of color stain, they have drawbacks, e.g., of generating colored matter after performing their function as color stain inhibitor and causing undesirable changes in photographic properties during preparation and storage of sensitive materials.

On the other hand, EP-A2-0338785, JP-A-03-164735 (the term "JP-A" as used herein means an "unexamined published Japanese patent application") and JP-A-05-232651 disclose the use of nondiffusible hydrazine compounds as color fog inhibitors. Although the nondiffusible hydrazine compounds disclosed therein include some phosphorylhydrazine compounds, those phosphorylhydrazine compounds have little effects on the inhibition of color fog. Therefore, introduction of further improvements in them has been requested. Further, JP-A-60-140340, JP-A-63-223744, JP-A-63-286840, JP-A-63-234244, JP-A-63-306438, JP-A-05-165134, JP-A-05-197091, JP-A-05-142688, JP-A-02-1834 and so on use hydrazine compounds as nucleation agent in photographic systems, and some phosphorylhydrazine compounds are presented therein. However, those compounds react directly with silver halides to cause alterations in photosensitivity. Accordingly, they cannot answer the purposes of the present invention. As for the use in systems other than the photographic system, U.S. Pat. No. 4,203,932 demonstrates that phosphorylhydrazines are effective insecticides. However, none of the above-cited references have any descriptions of the compounds having the structure according to the present invention, or the structure in which hydrazine moieties are attached directly to a phosphorus atom. Therefore, the compounds of the present invention have structural novelty, and it was unexpected that these compounds could solve the aforesaid problems in the photographic system.

SUMMARY OF THE INVENTION

A first object of the present invention is to provide a photosensitive material which is reduced in color stain and color fog and has excellent color reproducibility.

A second object of the present invention is to provide a photosensitive material which has slight changes in photographic properties during production and storage thereof.

A third object of the present invention is to provide compounds which enable the realization of the foregoing objects of providing photosensitive materials having the properties described above.

The above-described objects are attained with a silver halide color photosensitive material having on a support at least one photosensitive silver halide emulsion layer, said material containing at least one nondiffusible compound represented by the following formula (I), (I-1) or (I-2):

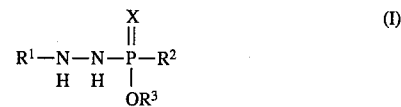

wherein $R^1$ represents an aryl group or a heterocyclic group, $R^2$ represents an alkyl group, a cycloalkyl group, an alkoxy group or an aryloxy group, $R^3$ represents an alkyl group, a cycloalkyl group, an aryl group or a heterocyclic group and X represents an oxygen atom or a sulfur atom; provided that $R^3$ does not represent a phenyl group when $R^2$ represents a phenoxy group:

wherein $R^1$ represents the same group as $R^1$ in the formula (I); $A^1$ and $A^2$ each represents a hydrogen atom or a hydrolyzable group; X represents the same atom as X in the formula (I); and $Y^1$ represents atoms completing a phosphorus atom-containing heterocyclic ring:

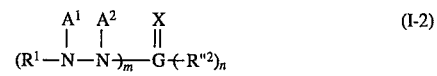

wherein $R^1$ represents the same group as $R^1$ in the formula (I); $R''^2$ represents an alkyl group, a cycloalkyl group, an aryl group, a heterocyclic group, an alkoxy group or an aryloxy group; $A^1$ and $A^2$ each represents the same meaning as $A^1$ and $A^2$ in the formula (I); G represents a carbon atom or a phosphorus atom; X represents the same atom as X in the formula (I); when G represents a carbon atom, m is 2 and n is 0; when G represents a phosphorus atom, m is 2 and n is 1, or m is 3 and n is 0; and when m is 2 or more, two or three $R^1N(A^1)N(A^2)$-groups may be the same or different.

DETAILED DESCRIPTION OF THE INVENTION

The compounds represented by formula (I) are described below in detail.

In formula (I), $R^1$ represents a substituted or unsubstituted aryl group or a substituted or unsubstituted heterocyclic group. The aryl groups preferred as $R^1$ are those containing 6 to 30 carbon atoms, such a phenyl and naphthyl groups. The heterocyclic groups preferred as $R^1$ are 3- to 8-membered ones which contain as hetero atom(s) an oxygen atom, a nitrogen atom or/and a sulfur atom, with specific examples including a 2-pyridyl group, a 2-furyl group, a 2-benzoxazolyl group and a 2-thienyl group. In particular, it is favorable for the present compound that $R^1$ is an aryl group.

As examples of substituent(s) which $R^1$ can have, mention may be made of alkyl group, aryl groups, acylamino groups (preferably, those containing 2 to 60 carbon atoms, e.g., acetylamino, n-butanoylamino, octanoylamino, 2-hexadecanoylamino, 2-(2',4'-di-t-amylphenoxy)butanoylamino, benzoylamino, nicotinoylamino), alkoxy groups (preferably, those containing 1 to 60 carbon atoms, e.g., methoxy, ethoxy, butoxy, n-octyloxy, hexadecyloxy, 2-methoxyethoxy), aryloxy groups (preferably, those containing 6 to 60 carbon atoms, e.g., phenoxy, 2,4-t-amylphenoxy, 4-t-butylphenoxy, naphthoxy), alkylthio groups (preferably, those containing 1 to 60 carbon atoms, e.g., methylthio, ethylthio, butylthio, hexadecylthio), arylthio groups (preferably, those containing 6 to 60 carbon atoms, e.g., phenylthio, 4-dodecyloxyphenylthio), acyl groups (preferably, those containing 1 to 60 carbon atoms, e.g., acetyl, benzoyl, butanoyl, dodecanoyl), sulfonyl groups (preferably, those containing 1 to 60 carbon atoms, e.g., methanesulfonyl, butanesulfonyl, toluenesulfonyl), sulfonylamino groups (preferably, those containing 1 to 60 carbon atoms, e.g., methanesulfonylamino, phenylsulfonylamino), a cyano group, an alkoxycarbonyl group (preferably, those containing 2 to 60 carbon atoms, e.g., ethoxycarbonyl, hexyloxycarbonyl, dodecyloxycarbonyl), an aryloxycarbonyl group (preferably, those containing 7 to 30 carbon atoms, e.g., phenoxycarbonyl, naphthyloxycarbonyl), carbamoyl groups (preferably, those containing 1 to 60 carbon atoms, e.g., N,N-dicyclohexylcarbamoyl), sulfamoyl groups (preferably, those containing 0 to 60 carbon atoms, e.g., N,N-dimethylsulfamoyl), a carboxyl group, halogen atoms and a hydroxyl group. Of these substituents, an alkyl group, an alkoxy group, an aryloxy group, an acylamino group and a sulfonylamino group are preferred over the others. In particular, an alkoxy group, an acylamino group and a sulfonylamino group are favorable.

The groups cited above as the substituents may be further substituted with one or more of the above-cited groups. Further, if possible, some of them may combine with each other to form a ring.

When $R^2$ represents an alkyl group, the alkyl group may be a substituted one or an unsubstituted one. Preferably, it is an alkyl group containing 1 to 60 carbon atoms, with preferable examples including a methyl group, an ethyl group, a propyl group, a iso-butyl group, a t-butyl group, a 2-ethylhexyl group, a nonyl group, an undecyl group, a pentadecyl group, a n-hexadecyl group and a 3-decanamidopropyl group. When $R^2$ represents a cycloalkyl group, the cycloalkyl group may be a substituted one or an unsubstituted one. Preferably, it is a cycloalkyl group containing 3 to 60 carbon atoms, with preferable examples including a cyclopropyl group, a 1-ethylcyclopropyl group, a cyclopentyl group and a cyclohexyl group. When $R^2$ represents an alkoxy group, specific examples of the alkyl moiety thereof include the same alkyl and cycloalkyl groups as instanced above. When $R^2$ represents an aryloxy group containing at least 7 carbon atoms, the aryl moiety thereof has the same meaning as the aryl group, including substituent(s) thereof, which $R^1$ represents. Of these groups, an alkoxy or aryloxy group is preferred as $R^2$. In particular, it is favorable for the present compound that $R^2$ is an alkoxy group.

As for the substituent(s) which $R^2$ can have, the groups instanced as substituents in the description of $R^1$ can be applied thereto. The groups preferred as substituent(s) of $R^2$ are an alkyl group, an alkoxy group, an aryloxy group, an acyl group and a hydroxyl group. In particular, an alkyl group, an alkoxy group and an acyl group are favorable over the others.

When $R^3$ represents an alkyl or cycloalkyl group, the group has the same meaning as the alkyl or cycloalkyl group cited in the description of $R^2$. When $R^3$ represents an aryl or heterocyclic group, the group has the same meaning as the aryl or heterocyclic group cited in the description of $R^1$. The groups preferred as $R^3$ are an alkyl group and an aryl group. Especially, an alkyl group is favored.

As for the substituent(s) which $R^3$ can have, the groups instanced as substituents in the description of $R^1$ can be applied thereto. The groups preferred as substituent(s) of $R^3$ are an alkyl group, an alkoxy group, an aryloxy group, an acyl group and a hydroxyl group. In particular, an alkyl group, an alkoxy group and an acyl group are favorable over the others.

It is preferable for at least one among $R^1$, $R^2$ and $R^3$ that a ballast group commonly used for nondiffusible photographic additives, such as couplers, be incorporated therein. Such a ballast group is a group containing at least 8 carbon atoms and has no adverse effect on photographic properties, and can be chosen from among, e.g., an alkyl group, an alkoxy group, an aryl group, an aryloxy group, an amido group, an ureido group, a sulfonamido group, an ester group, a sulfonyl group, an acyl group, a hydroxyl group and combinations of two or more thereof.

As for the combination of $R^1$, $R^2$ and $R^3$, preferred ones are the combination of $R^1$ which represents an aryl group, $R^2$ which represents an alkoxy group and $R^3$ which represents an alkyl group and the combination of $R^1$ which represents an aryl group, $R^2$ which represents an aryloxy group and $R^3$ which represents an aryl group, especially the former combination.

Specific examples of the present compound represented by general formula (I) are illustrated below. However, the present invention should not be construed as being limited to these exemplified compounds.

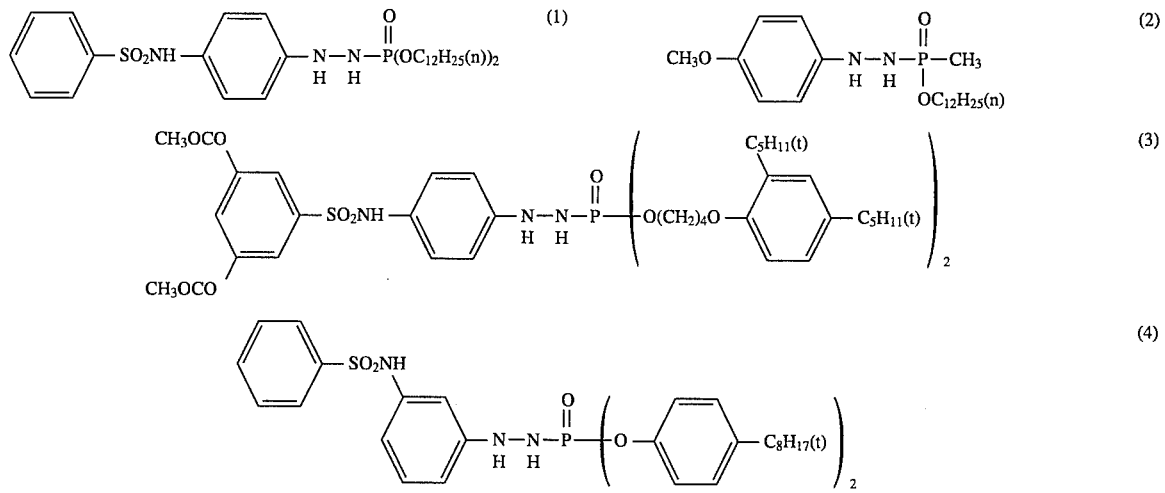

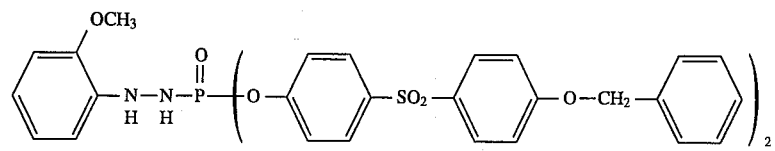
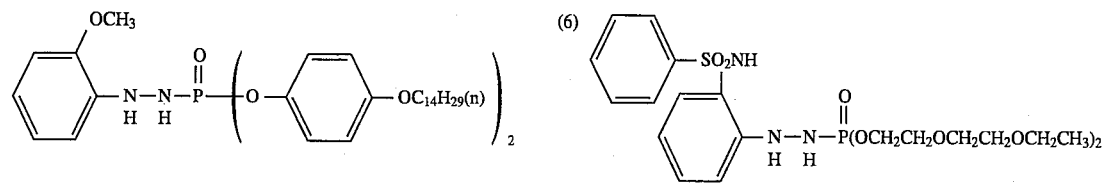
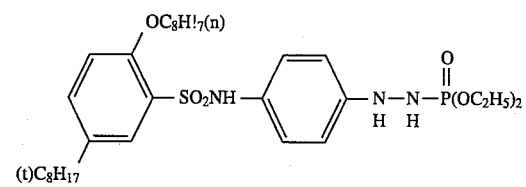
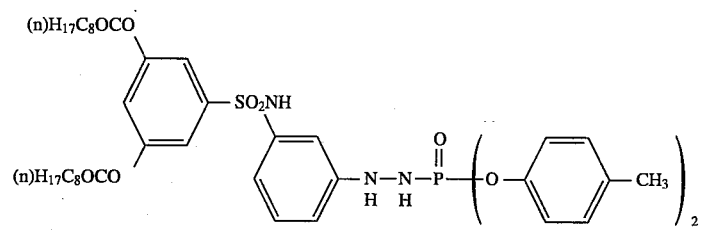
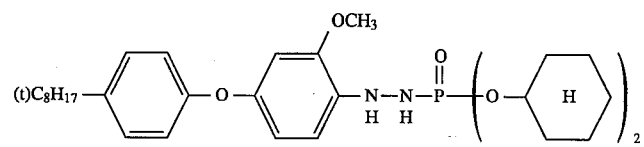
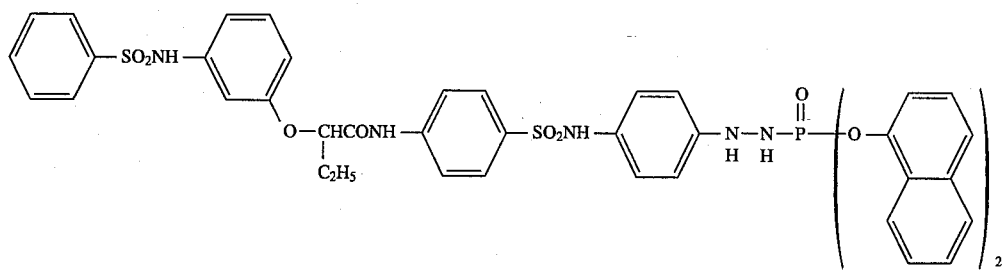
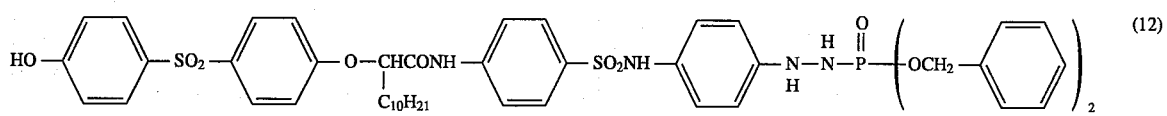
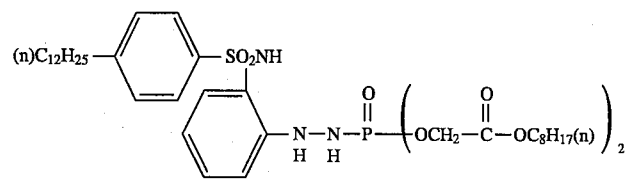
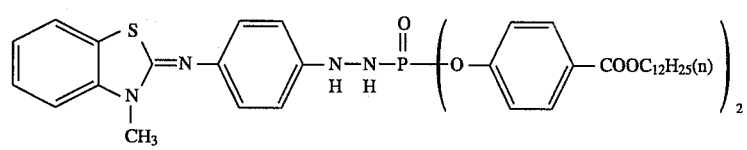

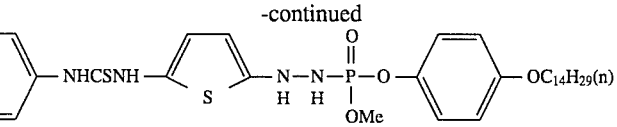
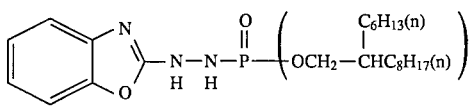
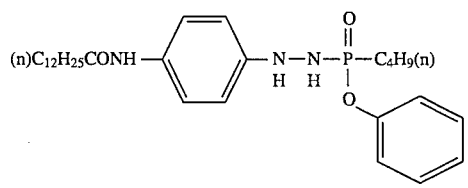
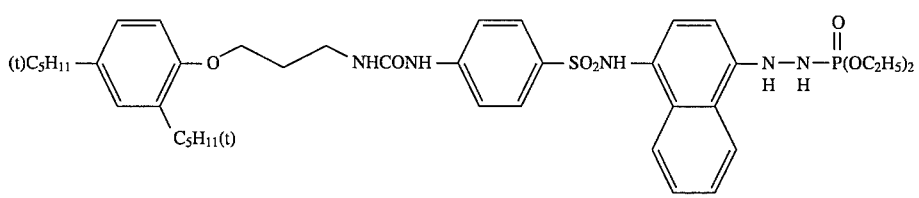
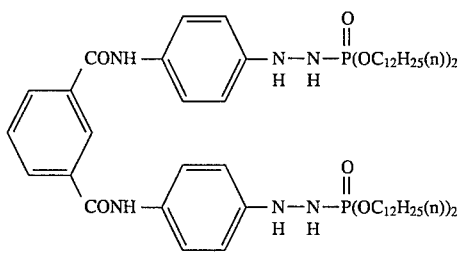
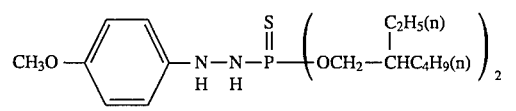
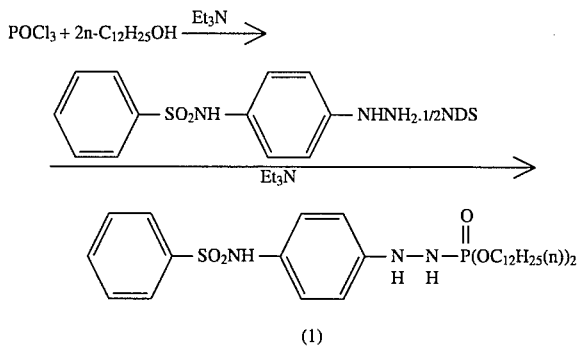

The present compounds represented by formula (I) can be synthesized using the same methods as adopted in the Syntheses described below or the methods following them.

1. Synthesis of Exemplified Compound (1) [Bis(dodecyloxy) p-phenylsulfonylaminohydrazidopbosphate]:

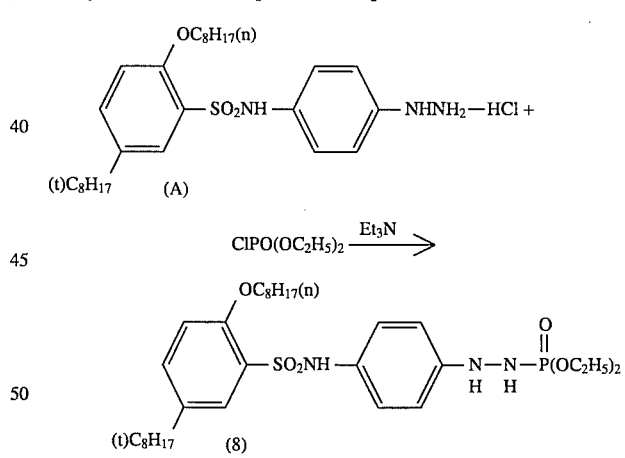

A solution of n-dodecanol (22.7 ml) and triethylamine (21 ml) in hexane (12 ml) was dripped slowly to a solution of phosphorus oxychloride (4.6 ml) in hexane (30 ml) at room temperature, and the resulting mixture was stirred for 2 hours. Thereto, 16.3 g of the naphthalene-1,5-disulfonic acid (abbreviated as "NDS") salt of p-phenylsulfonylaminophenylhydrazine and 7.0 ml of triethylamine were added, and stirred for 3 hours at room temperature. The reaction solution was added to 200 ml of water, extracted with ethyl acetate in a conventional manner, and then concentrated. The residue on concentration was purified by column chromatography on silica (developer: n-hexane/ethyl acetate mixture), crystallized from ethanol, and then dried. Thus, 20.2 g of the exemplified Compound (1) was obtained in a 61% yield.

$^1$H NMR (CDCl$_3$) 0.90 (t, 6H) 1.25 (m, 36H) 1.56 (m, 4H) 4.00 (m, 4H) 4.80 (d, 1H) 5.41 (s, 1H) 6.62 (s, 1H) 6.28 (d, 2H) 6.92 (d, 2H) 7.40 (m, 3H) 7.75 (m, 2H)

2. Synthesis of Exemplified Compound (8):

The hydrazine hydrochloride (A) in an amount of 7.0 g was dispersed into 50 ml of acetonitrile. Thereto were added 3.0 ml of diethylphosphoric acid chloride and 3.6 ml of triethylamine at room temperature, followed by 5 hours' stirring at room temperature. The reaction solution obtained was added to 100 ml of water, extracted with ethyl acetate in a conventional manner, and concentrated. The residue on concentration was purified by column chromatography on silica (developer: n-hexane/ethyl acetate mixture), crystallized from ethanol, and then dried. Thus, 6.6 g of the exemplified Compound (8) was obtained in a 80% yield.

$^1$H NMR (CDCl$_3$) 0.55 (s, 9H) 0.90 (t, 3H) 1.25 (m, 18H) 1.50 (s, 6H) 1.95 (m, 2H) 4.20 (m, 6H) 4.25 (d, 1H) 5.30 (s, 1H) 6.20 (m, 3H) 6.92 (m, 3H) 7.45 (m, 1H) 7.20 (m, 1H)

The compounds represented by formula (I-1) are described below in detail.

In formula (I-1), $R^1$ represents the same meaning as $R^1$ in the general formula (I).

In formula (I-1), $Y^1$ represents atoms completing a phosphorus atom-containing heterocyclic ring, preferably atoms completing a 5- to 10-membered phosphorus atom-containing heterocyclic ring which is constituted of carbon atoms and oxygen atom(s), nitrogen atom(s) or sulfur atom(s), and more preferably atoms comprising an alkylene group, an arylene group or a combination thereof.

As for the substituent(s) which $Y^1$ can have, the groups recited above as substituents of $R^1$ can be applied thereto. The groups more preferred as substituent(s) of $Y^1$ are an alkyl group, an alkoxy group, an aryloxy group, an acyl group, a alkoxycarbonyl group, an aryloxycarbonyl group, a carbamoyl group, a sulfonyl group, a sulfamoyl group, a cyano group, a carboxyl group and a hydroxyl group. In particular, an alkyl group, an alkoxy group and an alkyloxycarbonyl group are favorable over the others.

When $A^1$ and $A^2$ represent hydrolyzable groups, sulfonyl, acyl and oxalyl groups are examples thereof. As for $A^1$ and $A^2$, however, hydrogen atoms are preferable.

It is desirable that a ballast group commonly used for nondiffusible photographic additives, such as couplers, be introduced into at least either $R^1$ or $Y^1$. Such a ballast group is a group containing at least 8 carbon atoms and has no adverse effect on photographic properties, and can be chosen from among, e.g., an alkyl group, an alkoxy group, an aryl group, an aryloxy group, an amido group, an ureido group, a sulfonamido group, an ester group, a sulfonyl group, an acyl group, a hydroxyl group and combinations of two or more thereof.

Of the compounds represented by formula (I-1), compounds represented by the following formula (II-1) are preferred over the others:

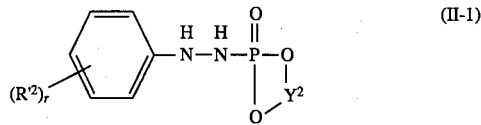

where $R'^2$ represents a substituent group, r is an integer of from 0 to 5, and $Y^2$ represents atoms completing a 5- to 10-membered heterocyclic ring which comprises a —O—(PO)—O— linkage and carbon atoms.

Suitable examples of a substituent group represented by $R'^2$ include the groups recited above as examples of the substituent(s) of $R^1$. Of those groups, an acylamino group, a sulfonamido group, an alkoxy group, an alkyl group and a chlorine atom are preferred as $R'^2$ over the others.

r in formula (II-1) is preferably 1, 2 or 3, and more preferably 1.

$Y_2$ is preferably atoms completing a 5-, 6- or 7-membered heterocyclic ring which is constituted of a —O—(PO)—O— linkage and carbon atoms, and more preferably atoms completing a 5-, 6- or 7-membered heterocyclic ring which is constituted of an —O—(PO)—O— linkage and an alkylene group, an arylene group or a combination thereof. Further, such atoms may be substituted with any of the groups recited as substituent(s) of $R^1$ in formula (I-1). Preferably, group(s) with which the atoms may be substituted include an alkyl group, an alkoxy group, an aryloxy group, a halogen atom, an aryl group and an alkoxycarbonyl group. Of these groups, an alkoxy group and an alkoxycarbonyl group are favored over the others.

The compounds of formula (I), (I-1) and (I-2) are prepared by a reaction of corresponding phosphorus chloride with hydrozine under a presence of basic compound, according to the process disclosed, for example, in Aust. J. Chem. 27, 1065, 1979, and 28, 669, 1975, Chem. Ind. (London) 1828, 1962 and J. Med. Chem. 35, 1650, 1992.

Specific examples of the present compound represented by general formula (I-1) are illustrated below. However, the invention should not be construed as being limited to these exemplified compounds.

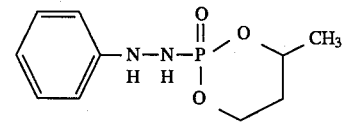

(1)'

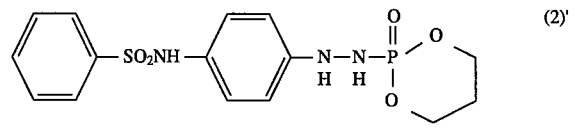

(2)'

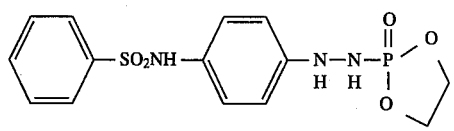

(3)'

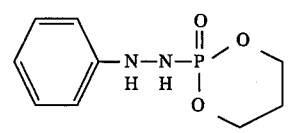

(4)'

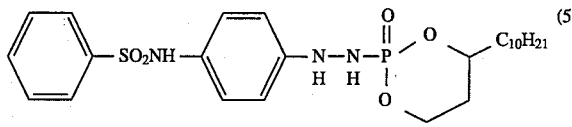

(5)'

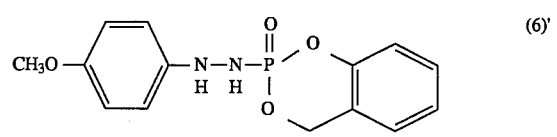

(6)'

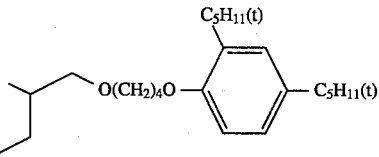

(7)'

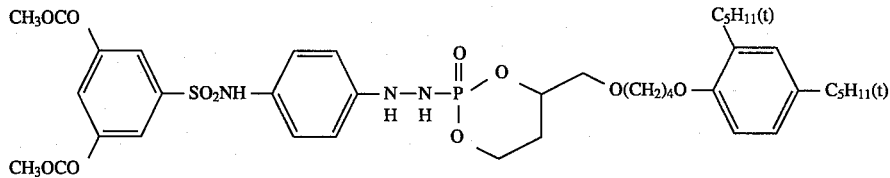

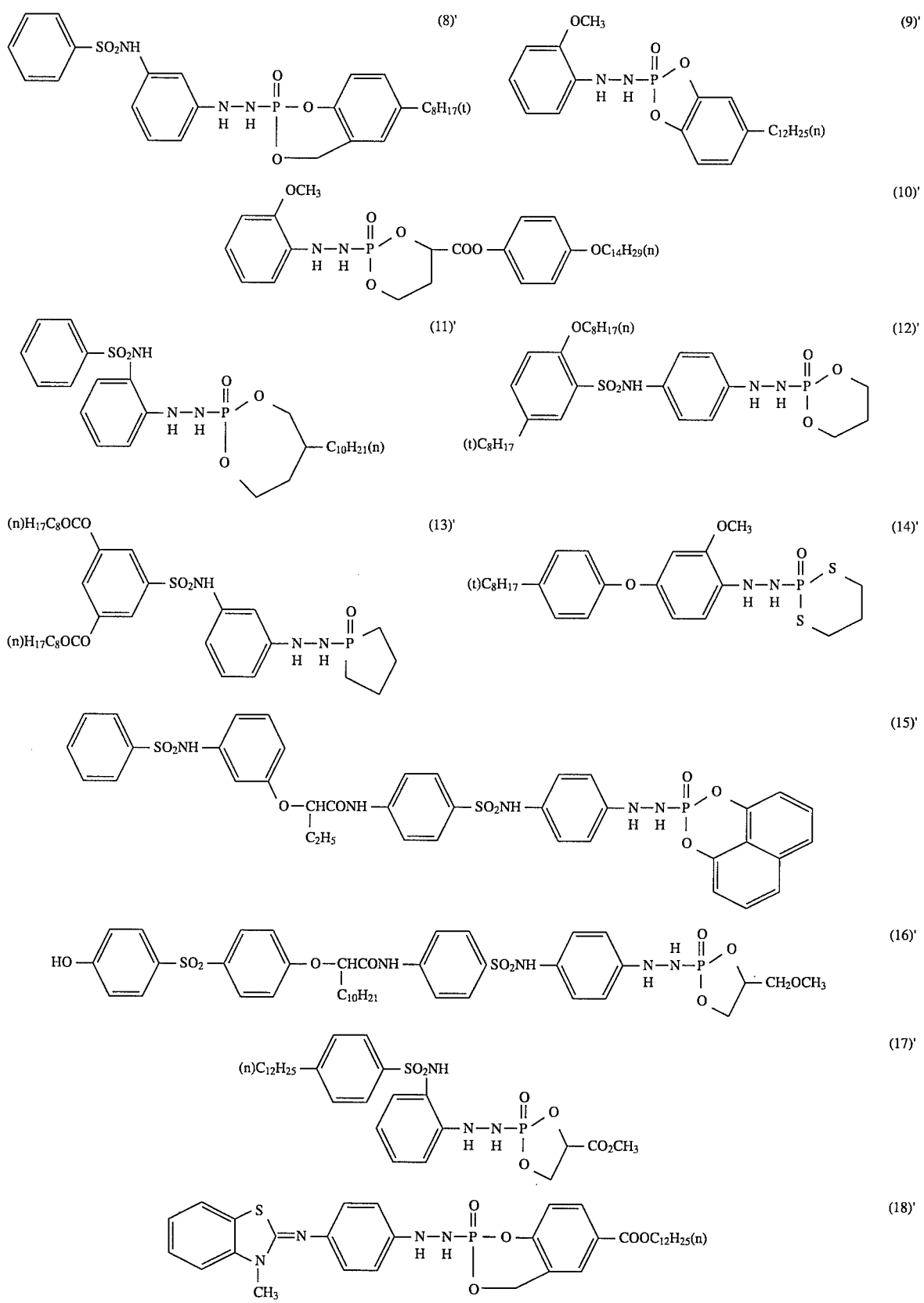

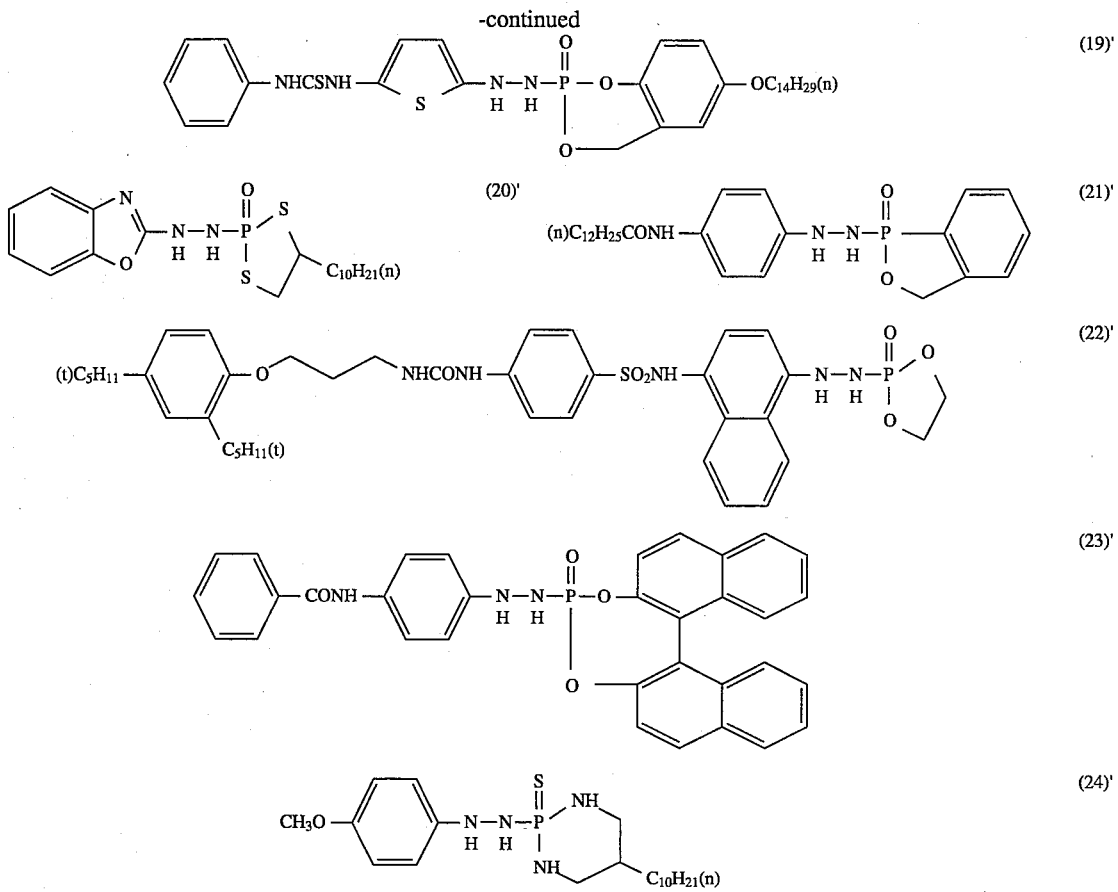

Typical synthesis examples of compounds represented by the formula (I-1) according to the present invention and identification data thereof are shown below.

Synthesis Example 1

Synthesis of 2-[4-(Phenylsulfonylamino)phenylhydrazino]-1,3-dioxaphospholane-2-oxide (Exemplified Compound (3)'):

1,5-Naphthalenedisulfonic acid salt of 4-(phenylsulfonylamino)phenylhydrazine in an amount of 4.1 g was dispersed into 30 ml of dimethylacetamide, admixed with 2.1 g of 2-chloro-1,3-dioxaphospholane-2-oxide and 2.8 ml of triethylamine, and then stirred for 5 hours at room temperature. The resulting solution was added to 100 ml of water, and extracted with ethyl acetate in the usual way. The extract thus obtained was concentrated, and the residue thereof was purified by column chromatography on silica gel (developer: a n-hexane/ethyl acetate mixture), crystallized from ethanol, and then dried. Thus, 2.2 g of the exemplified Compound (3)' was obtained in a 51% yield.

Synthesis Example 2

Synthesis of 4-Decyl-2-[4-(phenylsulfonylamino)phenylhydrazino]-1,3-dioxaphosphane-2-oxide (Exemplified Compound (5)'):

A solution of 1,3-tridecanediol (4.3 g) in methylene chloride (10 ml) was dripped slowly into a solution of phosphorus oxychloride (1.8 ml) in methylene chloride (30 ml) at room temperature, and heated with stirring under reflux for 4 hours. After cooling to room temperature, the reaction solution was admixed with 8.1 g of 1,5-naphthalenedisulfonic acid salt of 4-phenylsulfonylaminophenylhydrazine and 5.6 ml of triethylamine, and then stirred for 5 hours at room temperature. The resulting solution was added to 200 ml of water, and extracted with ethyl acetate in the usual way. The extract thus obtained was concentrated, and the residue thereof was purified by column chromatography on silica gel (developer: a n-hexane/ethyl acetate mixture), crystallized from ethanol, and then dried. Thus, 6.6 g of the exemplified Compound (5)' was obtained in a 61% yield.

Other compounds according to the present invention can be synthesized in the same manner as described above or a manner according thereto.

The identification data (NMR analysis and melting point (mp.) data) of five compounds thus synthesized are shown in Table 1-(1).

TABLE 1-(1)

| Compound No. | $^1$H NMR (CDCl$_3$) | mp. (°C.) |
|---|---|---|
| (1)' | 1.30 (d, J=7Hz, 3H), 1.60–2.15 (m, 2H), 4.15–4.55 (m, 2H), 4.60–4.80 (m, 1H), 5.55 (d, J=36Hz, 1H), 6.80–7.10 (m, 3H), 7.10–7.40 (m, 2H) | 151–154 |
| (2)' | 1.30 (d, J=7Hz, 3H), 1.65–2.10 (m, 2H), 4.10–4.55 (m, 2H), 4.60–4.80 (m, 1H), 5.90 (d, J=34Hz, 1H), 6.00 (s, 1H), 6.75 (d, J=8Hz, 2H), 6.95 (d, J=8Hz, 2H), 7.35–7.55 (m, 3H), 7.70–7.80 (m, 2H), 9.15 (s, 1H) | 226–228 |
| (3)' | 4.00–4.55 (m, 4H), 5.90 (d, J=34Hz, 1H), 6.00 (s, 1H), 6.60 (d, J=8Hz, 2H), 6.80 (d, J=8Hz, 2H), 7.30–7.60 (m, 3H), 7.60–7.70 (m, 2H), 9.70 (s, 1H) | 189–192 |
| (4)' | 1.90–2.20 (m, 2H), 4.30–4.60 (m, 4H), 5.10 (d, J=34Hz, 1H), 5.50 (s, 1H), 6.85– | 212–215 |

TABLE 1-(1)-continued

| Compound No. | $^1$H NMR (CDCl$_3$) | mp. (°C.) |
|---|---|---|
| (5)' | 7.00 (m, 3H), 7.20–7.35 (m, 2H) 0.90 (t, J=7Hz, 3H), 1.25 (m, 18H), 1.56 (m, 2H), 4.20 (m, 2H), 4.75 (s, 1H), 4.80 (d, J=33Hz, 1H), 5.41 (s, 1H), 6.62 (s, 1H), 6.28 (d, J=8Hz, 2H), 6.92 (d, J= 8Hz, 2H), 7.30–7.50 (m, 3H), 7.70–7.85 (m, 2H), 9.20 (s, 1H) | 180–183 |

The present compounds may be used as a combination of two or more thereof. The present compounds may be used in combination of two or more thereof.

Compounds represented by formula (I-2) are described below in detail.

In formula (I-2), $R^1$ represents the same meaning as $R^1$ in the formula (I).

When $R''^2$ represents an alkyl group, the alkyl group may be a substituted one or an unsubstituted one. Preferably, it is an alkyl group containing 1 to 60 carbon atoms, with specific examples including a methyl group, an ethyl group, a propyl group, an iso-butyl group, a tert-butyl group, a 2-ethylhexyl group, a nonyl group, an undecyl group, a pentadecyl group, a n-hexadecyl group and a 3-decanoylamidopropyl group. When $R''^2$ represents a cycloalkyl group, the cycloalkyl group may be a substituted one or an unsubstituted one. Preferably, it is a cycloalkyl group containing 3 to 60 carbon atoms, with specific examples including a cyclopropyl group, a 1-ethylcyclopropyl group, a cyclopentyl group and a cyclohexyl group. When $R''^2$ is an aryl group, examples of its aryl moiety include the aryl groups instanced in the description of $R^1$, excluding a phenyl group, and examples of its substituent part include the same groups as recited in the description of substituent(s) which $R^1$ can have. When $R''^2$ is a heterocyclic group, examples of its heterocyclic moiety include the heterocyclic groups instanced in the description of $R^1$, and examples of its substituent part include the same groups as recited in the description of substituent(s) which $R^1$ can have.

Each of the groups represented by $R^1$ may have substituent(s), and to such substituent(s) can be applied the groups recited above as the substituent(s) which $R^1$ can have. As examples of more preferable groups as the substituent(s), mention may be made of an alkyl group, an alkoxy group, an aryloxy group, an acyl group, an alkoxycarbonyl group, an aryloxycarbonyl group, a carbamoyl group, a sulfonyl group, a sulfamoyl group, a cyano group, a carboxyl group and a hydroxyl group. Of these groups, an alkyl group, an alkoxy group and an alkyloxycarbonyl group are favored in particular.

As for the hydrolyzable groups represented by $A^1$ and $A^2$, a sulfonyl group, an acyl group and an oxazolyl group are specific examples thereof. However, hydrogen atoms are preferred as $A^1$ and $A^2$.

It is preferable for at least either $R^1$ or $R''^2$ that a ballast group commonly used for nondiffusible photographic additives, such as couplers, be incorporated therein. Such a ballast group is a group containing at least 8 carbon atoms and has no adverse effect on photographic properties, and can be chosen from among, e.g., an alkyl group, an alkoxy group, an aryl group, an aryloxy group, an amido group, an ureido group, a sulfonamido group, an ester group, a sulfonyl group, an acyl group, a hydroxyl group and combinations of two or more thereof.

As for the combination of $R^1$ and $R''^2$, a case in which both are aryl groups is desirable.

Of the compounds represented by formula (I-2), those represented by the following formula (II-2) are preferred over the others:

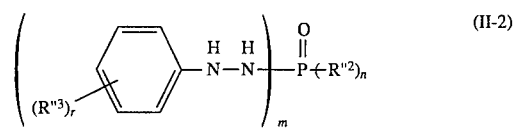

(II-2)

wherein $R''^2$ has the same meaning as $R''^2$ in formula (I-2); m is 2 or 3; n is 1 when m is 2, and n is 0 when m is 3; r is an integer from 0 to 5; and $R''^3$ represents a substituent, and when r represents 2 or more, a plurality of $R''^3$ groups may be the same or different.

Examples of a substituent preferred as $R''^3$ in formula (II-2) include those recited as substituent(s) which $R^1$ in formula (I-2) can have. More preferably, $R''^3$ is an acylamino group, a sulfonamido group, an alkoxy group, an alkyl group or a chlorine atom.

r in formula (II-2) is preferably 1, 2 or 3.

Of the compounds represented by formula (II-2), compounds represented by formula (III-2) are preferred over the others:

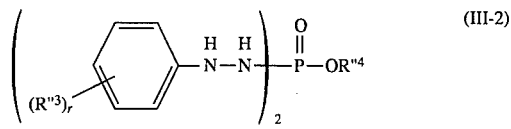

(III-2)

wherein $R''^4$ represents an alkyl group or an aryl group, and $R''^3$ and r have the same meanings as $R''^3$ and r in the formula (II-2) respectively.

The alkyl or aryl group represented by $R''^4$ is preferably chosen from those cited as examples of an alkyl or aryl group represented by $R''^2$ in formula (I-2).

As for the alkyl group represented by $R''^4$, a secondary alkyl or cycloalkyl group containing 3 to 30 carbon atoms is more preferred.

As for the aryl group represented by $R''^4$, a substituted or unsubstituted phenyl group is more preferred. Examples of group(s) by which the phenyl group may be substituted include those recited above as substituent(s) which $R^1$ in formula (I-2) can have. Of those substituent groups, an alkyl group (including those containing 1 to 16 carbon atoms, such as methyl, isopropyl, tert-butyl, 2-ethylhexyl, cyclohexyl, dodecyl, etc.), an alkoxy group (including those containing 1 to 16 carbon atoms, such as methoxy, isopropoxy, cyclohexyloxy, hexadecyloxy, etc.) and a halogen atom (e.g, chlorine, bromine, fluorine) are preferred over the others.

In formula (III-2), it is preferable for r to be 1.

Specific examples of the present compound represented by formula (I-2) are illustrated below. However, the invention should not be construed as being limited to these exemplified compounds.

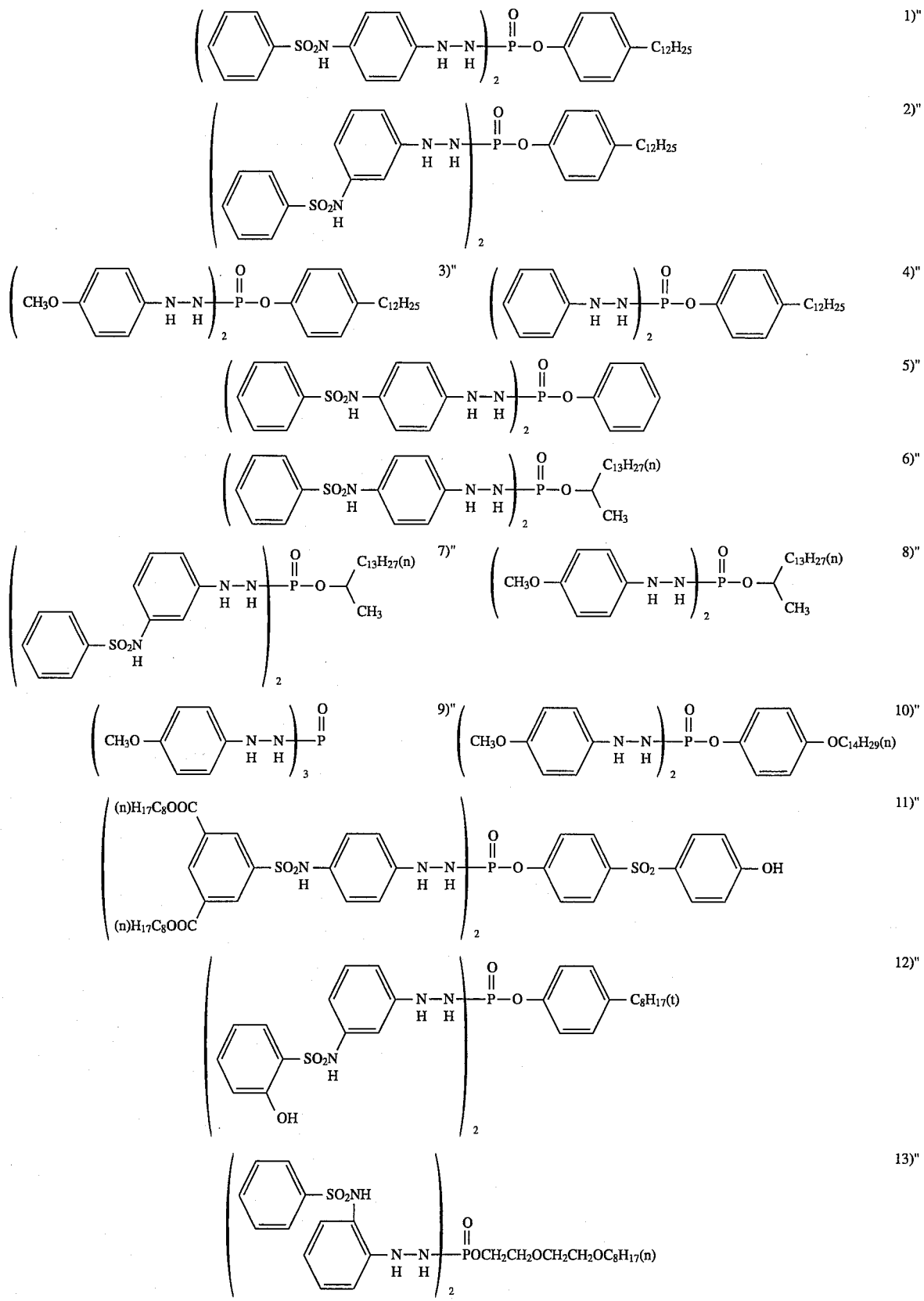

-continued
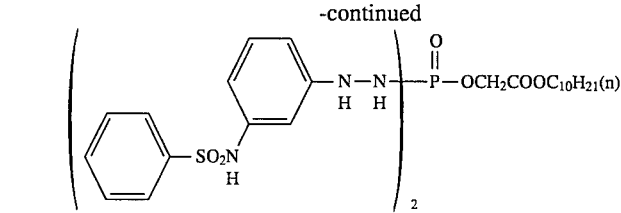
14)"
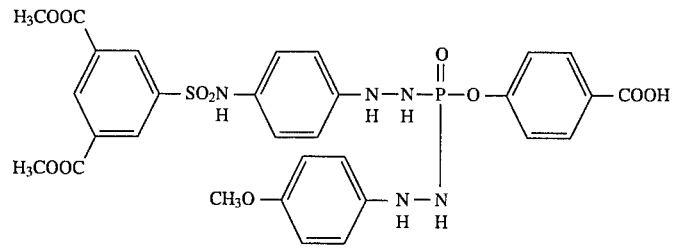
15)"
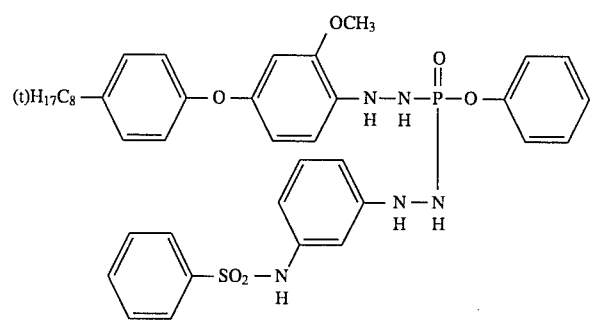
16)"
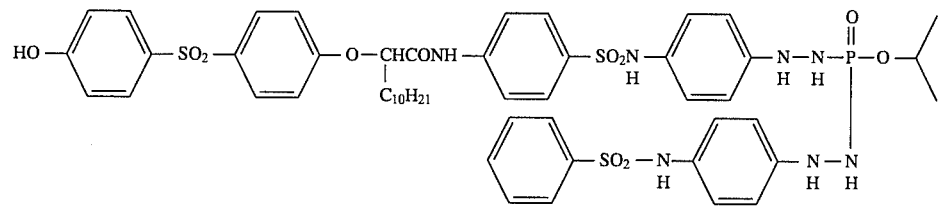
17)"
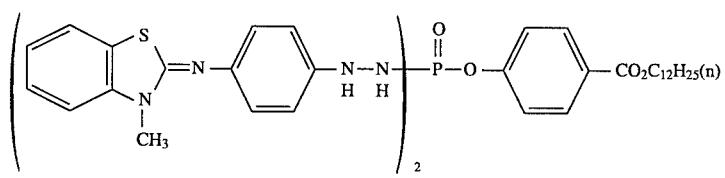
18)"
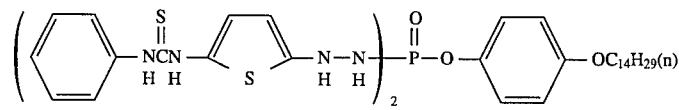
19)"
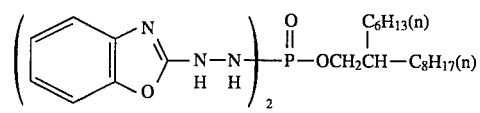
20)"
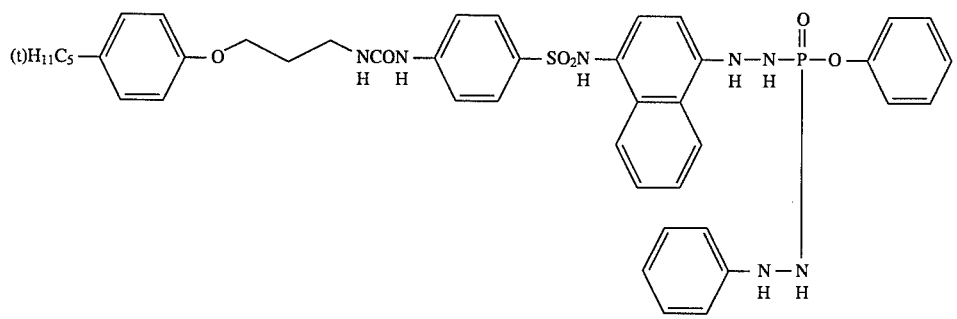
21)"

-continued

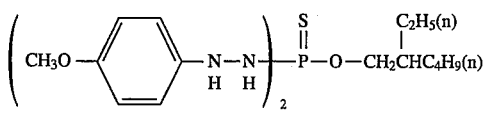 22)"
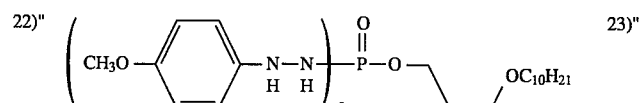 23)"

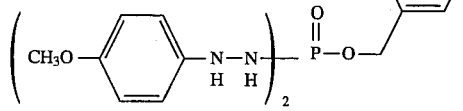

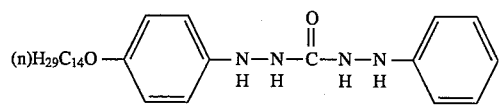 24)"

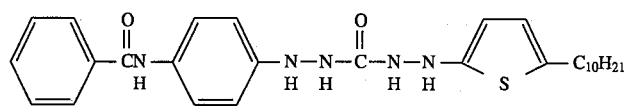 25)"

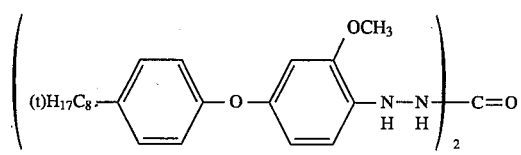 26)"

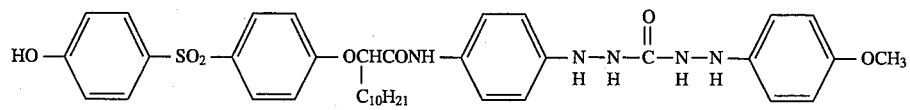 27)"

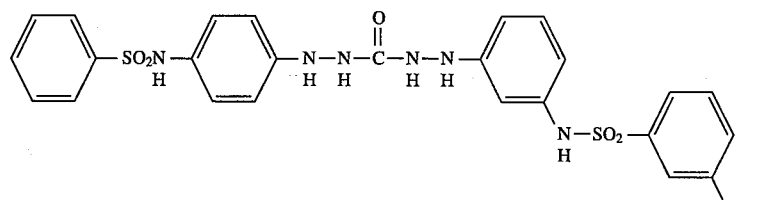 28)"

Typical synthesis examples of compounds of formula (I-2) according to the present invention and identification data thereof are shown below.

Synthesis Example 1

Synthesis of 2-Pentadecyl bis[(4-(phenylsulfonylamino)phenylhydrazido]phosphate (Exemplified Compound (6)"):

A solution containing 4.6 ml of phosphorus oxychloride in 50 ml of methylene chloride was dripped into a solution containing 11.3 ml of 2-pentadecanol in 20 ml of methylene chloride at 0° C., and stirred for 3 hours at room temperature. The resulting solution was admixed with 33.0 g of 4-(phenylsulfonylamino)phenylhydrazine 1,5-naphthalenedisulfonate and 14 ml of triethylamine, and stirred for 5 hours at room temperature. The reaction solution was admixed with 100 ml of water, and extracted with ethyl acetate in the usual way. The extract thus obtained was concentrated, and the residue thereof was purified by column chromatography on silica gel (developer: a n-hexane/ethyl acetate mixture). Thus, 12.8 g of the exemplified Compound (6)" was obtained in a 78% yield.

Synthesis Example 2

Synthesis of Phosphorus tri(4-methoxyphenylhydrazide) (Exemplified Compound (9)"):

5.1 g of 4-methoxyphenylhydrazine hydrochloride and 6 ml of triethylamine was added to a solution of phosphorus oxychloride (0.92 ml) in methylene chloride (50 ml), and stirred for 5 hours at room temperature. The reaction solution was admixed with 100 ml of water, and extracted with ethyl acetate in the usual way. The extract thus obtained was concentrated, and the residue thereof was purified by column chromatography on silica gel (developer: a n-hexane/ethyl acetate mixture), crystallized from ethanol, and then dried. Thus, 3.4 g of the exemplified Compound (9)" was obtained in a 77% yield.

Other compounds according to the present invention can be synthesized in the same manner as described above or a manner according thereto.

The identification data (NMR analysis and melting point (mp.) data) of 9 compounds thus synthesized are shown in Table 1.

TABLE 1-2

| Compound No. | $^1$H NMR (CDCl$_3$) | mp. (°C.) |
| --- | --- | --- |
| (1)" | 0.60–1.80 (m, 25H), 6.30 (d, J=34Hz, 2H), 6.50 (s, 2H), 6.70 (d, J=7Hz, 4H), 6.85 (d, J=7Hz, 4H), 7.00–7.30 (m, 3H), 7.35–7.55 (m, 6H), 7.65–7.80 (m, 4H), 9.35 (s, 2H) | oily matter |

TABLE 1-2-continued

| Compound No. | $^1$H NMR (CDCl$_3$) | mp. (°C.) |
|---|---|---|
| (2)" | 0.60–1.90 (m, 25H), 5.80 (d, J=36Hz, 2H), 6.30 (s, 2H), 6.70–7.05 (m, 3H), 7.10–7.70 (m, 6H), 7.70–7.95 (m, 4H), 9.35 (s, 2H) | oily matter |
| (3)" | 0.62–2.00 (m, 25H), 3.70 (s, 6H), 5.70 (d, J=33Hz, 2H), 5.90 (s, 2H), 6.70 (d, J=7Hz, 4H), 7.05–7.30 (m, 4H) | oily matter |
| (4)" | 6.45 (d, J=33Hz, 2H), 6.80 (s, 2H), 6.55–6.70 (m, 4H), 6.80–7.00 (m, 4H) | oily matter |
| (5)" | 6.30 (d, J=34Hz, 2H), 6.50 (s, 2H), 6.70 (d, J=7Hz, 4H), 6.85 (d, J=7Hz, 4H), 7.00–7.30 (m, 6H), 7.35–7.55 (m, 5H), 7.65–7.80 (m, 4H), 9.35 (s, 2H) | oily matter |
| (6)" | 0.80–2.20 (m, 27H), 1.30 (d, J=7Hz, 3H), 4.00–4.20 (m, 1H), 6.30 (d, J=34Hz, 2H), 6.50 (s, 2H), 6.65 (d, J=7Hz, 4H), 6.80 (d, J=7H$_z$, 4H), 7.35–7.55 (m, 6H), 7.65–7.80 (m, 4H), 9.30 (s, 2H) | 164–168 |
| (7)" | 0.80–2.20 (m, 27H), 1.30 (d, J=7Hz, 3H), 4.00–4.20(m, 1H), 6.70–7.05 (m, 8H), 7.10–7.70 (m, 6H), 7.70–7.95 (m, 4H), 9.40 (s, 2H) | oily matter |
| (8)" | 0.80–2.20 (m, 27H), 1.30 (d, J=7Hz, 3H), 4.00–4.20 (m, 1H), 5.70 (d, J=33Hz, 2H), 5.90 (s, 2H), 6.75 (d, J=7Hz, 4H), 6.85 (d, J=7Hz, 4H) | oily matter |
| (9)" | 3.80 (s, 9H), 5.75 (d, J=33Hz, 3H), 5.95 (s, 3H), 6.60 (d, J=7Hz, 6H), 6.70 (d, J=7Hz, 6H) | 177–180 |

The present compounds may be used in combination of two or more thereof.

The present compounds can be incorporated in at least one constituent layer of a photosensitive material, e.g., a protective layer, a light-sensitive silver halide emulsion layer, a light-insensitive fine grain silver halide emulsion layer, an interlayer, a filter layer, an undercoat layer, an antihalation layer or so on. Preferably, they are used in a light-sensitive emulsion layer and/or an interlayer arranged between two light-sensitive emulsion layers (which may be the same or different in color sensitivity). Especially, it is effective to use them in the interlayer described above, preferably in an amount of 5 to 2,000 mg/m$^2$.

When the present compounds are added to a light-insensitive layer, it is desirable that the gelatin coverage of the light-insensitive layer be in the range of 0.2 to 2.0 g/m$^2$, preferably 0.3 to 1.2 g/m$^2$, and particularly preferably 0.4 to 1.0 g/m$^2$.

The present compounds can be incorporated in an intended layer through the addition to a coating composition for that layer as they are or in the form of solution in a low boiling point organic solvent having no influence upon a silver halide photosensitive material, such as alcohols (e.g., methyl alcohol). In adding them, they may be dispersed in a polymer latex, or a polymer may be impregnated therewith. Also, they may be dissolved in a high boiling point organic solvent, and then dispersed in the form of emulsion into a water solution.

The total amount of the present compound of (I), (I-1) or (I-2) added to a photosensitive material ranges generally from 0.001 to 0.8 g/m$^2$, preferably from 0.005 to 0.5 g/m$^2$, and particularly preferably from 0.01 to 0.3 g/m$^2$.

Various arts and a wide variety of inorganic and organic materials described in *Research Disclosure* No. 308119 (1989) are generally applicable to the present silver halide photographic materials.

More specifically, arts and materials (including inorganic and organic ones) which can be applied to the color photosensitive materials using the present silver halide photosensitive emulsion are described, e.g., at the following pages in EP-A2-0436938 and other European Patents cited below.

| Item | Passage corresponding thereto |
|---|---|
| 1) Layer structure | page 146, line 34, to page 147, line 25 |
| 2) Silver halide emulsion | page 147, line 26, to page 148, line 12 |
| 3) Yellow coupler | page 137, line 35, to page 146, line 33; and page 149, lines 21–23 |
| 4) Magenta coupler | page 149, lines 24–28; and EP-A1-0421453, page 3, line 5, to page 25, line 55 |
| 5) Cyan coupler | page 149, lines 29–33; and EP-A2-043804, page 3, line 28, to page 40, line 2 |
| 6) Polymer coupler | page 149, lines 34–38; and EP-A2-0435334, page 113, line 39, to page 123, line 37 |
| 7) Colored coupler | page 53, line 42, to page 137, line 34; and page 149, lines 39–45 |
| 8) Other functional couplers | page 5, line 1, to page 53, line 41; page 149, line 46, to page 150, line 3; and EP-A2-0435334, page 3, line 1, to page 29, line 50 |
| 9) Antiseptics and antifungal agents | page 150, lines 25–28 |
| 10) Formaldehyde scavenger | page 149, lines 15–17 |
| 11) Other additives | page 153, lines 38–47; and EP-A1-0421453, page 75, line 21, to page 84, line 56, and page 27, line 40, to page 37, line 40 |
| 12) Dispersion method | page 150, lines 4–24 |
| 13) Support | page 150, lines 32–34 |
| 14) Thickness and physical properties of film | page 150, lines 35–49 |
| 15) Color development process | page 150, line 50, to page 151, line 47 |
| 16) Desilvering process | page 151, line 48, to page 152, line 53 |
| 17) Automatic developing machine | page 152, line 54, to page 153, line 2 |
| 18) Washing.Stabilization process | page 153, lines 3–37 |

The present invention will now be illustrated in more detail by way of the following examples. However, the invention should not be construed as being limited to these examples.

EXAMPLE 1

Preparation of Sample No. 101

On a 127 μm-thick cellulose triacetate film support provided with an undercoat, various photographic constituent layers having the compositions described below were coated to prepare a multilayer color photosensitive material (Sample No. 101). Each figure on the right side designates the amount of each ingredient added per m$^2$. Additionally, the effect of each ingredient added should not be construed as being limited to the described use.

| First layer (antihalation layer): | |
|---|---|
| Black colloidal silver | 0.10 g |
| Gelatin | 1.90 g |
| Ultraviolet absorbent U-1 | 0.10 g |
| Ultraviolet absorbent U-3 | 0.040 g |
| Ultraviolet absorbent U-4 | 0.10 g |
| High boiling point organic solvent Oil-1 | 0.10 g |
| Microcrystalline solid dispersion of Dye E-1 | 0.10 g |

Second layer (Interlayer):

| | |
|---|---|
| Gelatin | 0.40 g |
| Compound Cpd-C | 5.0 mg |
| Compound Cpd-J | 5.0 mg |
| Compound Cpd-K | 3.0 mg |
| High boiling point organic solvent Oil-3 | 0.10 g |
| Dye D-4 | 0.80 mg |

Third layer (Interlayer):

| | |
|---|---|
| Surface- and interior-fogged fine-grain silver iodobromide emulsion (having an average grain size of 0.06 μm, a variation coefficient of 18% with respect to grain size distribution, and an iodide content of 1 mole %) | 0.050 g, based on Ag |
| Yellow colloidal silver | 0.030 g, based on Ag |
| Gelatin | 0.40 g |

Fourth layer (low-speed red-sensitive emulsion layer):

| | |
|---|---|
| Emulsion A | 0.30 g, based on Ag |
| Emulsion B | 0.20 g, based on Ag |
| Gelatin | 0.80 g |
| Coupler C-1 | 0.15 g |
| Coupler C-2 | 0.050 g |
| Coupler C-3 | 0.050 g |
| Coupler C-9 | 0.050 g |
| Compound Cpd-C | 5.0 mg |
| Compound Cpd-J | 5.0 mg |
| High boiling point organic solvent Oil-2 | 0.10 g |
| Additive P-1 | 0.10 g |

Fifth layer (medium-speed red-sensitive emulsion layer):

| | |
|---|---|
| Emulsion B | 0.20 g, based on Ag |
| Emulsion C | 0.30 g, based on Ag |
| Gelatin | 0.80 g |
| Coupler C-1 | 0.20 g |
| Coupler C-2 | 0.050 g |
| Coupler C-3 | 0.20 g |
| High boiling point organic solvent Oil-2 | 0.10 g |
| Additive P-1 | 0.10 g |

Sixth layer (high-speed red-sensitive emulsion layer):

| | |
|---|---|
| Emulsion D | 0.40 g, based on Ag |
| Gelatin | 1.10 g |
| Coupler C-1 | 0.30 g |
| Coupler C-2 | 0.10 g |
| Coupler C-3 | 0.70 g |
| Additive P-1 | 0.10 g |

Seventh layer (intermediate layer):

| | |
|---|---|
| Gelatin | 0.50 g |
| Additive M-1 | 0.25 g |
| Dye D-5 | 0.020 g |
| Dye D-6 | 0.010 g |
| Compound Cpd-J | 5.0 mg |
| High boiling point organic solvent Oil-3 | 0.020 g |

Eighth layer (intermediate layer):

| | |
|---|---|
| Surface- and interior-fogged fine-grain silver iodobromide emulsion (having an average grain size of 0.06 μm, a variation coefficient of 16% with respect to grain size distribution, and an iodide content of 0.3 mole %) | 0.020 g, based on Ag |
| Yellow colloidal silver | 0.020 g, based on Ag |
| Gelatin | 0.80 g |
| Additive P-1 | 0.20 g |
| Color mixing inhibitor Cpd-A | 0.20 g |

Ninth layer (low-speed green-sensitive emulsion layer):

| | |
|---|---|
| Emulsion E | 0.10 g, based on Ag |
| Emulsion F | 0.30 g, based on Ag |
| Emulsion G | 0.20 g, based on Ag |
| Gelatin | 0.50 g |
| Coupler C-4 | 0.10 g |
| Coupler C-7 | 0.050 g |
| Coupler C-8 | 0.10 g |
| Compound Cpd-B | 0.030 g |
| Compound Cpd-D | 0.020 g |
| Compound Cpd-E | 0.020 g |
| Compound Cpd-F | 0.040 g |
| Compound Cpd-J | 10 mg |
| High boiling point organic solvent Oil-1 | 0.10 g |
| High boiling point organic solvent Oil-2 | 0.10 g |

Tenth layer (medium-speed green-sensitive emulsion layer):

| | |
|---|---|
| Emulsion G | 0.30 g, based on Ag |
| Emulsion H | 0.10 g, based on Ag |
| Gelatin | 0.60 g |
| Coupler C-4 | 0.070 g |
| Coupler C-7 | 0.050 g |
| Coupler C-8 | 0.050 g |
| Compound Cpd-B | 0.030 g |
| Compound Cpd-D | 0.020 g |
| Compound Cpd-E | 0.020 g |
| Compound Cpd-F | 0.050 g |
| High boiling point organic solvent Oil-2 | 0.010 g |

Eleventh layer (high-speed green-sensitive emulsion layer):

| | |
|---|---|
| Emulsion I | 0.50 g, based on Ag |
| Gelatin | 1.00 g |
| Coupler C-4 | 0.20 g |
| Coupler C-7 | 0.10 g |
| Coupler C-8 | 0.050 g |
| Compound Cpd-B | 0.080 g |
| Compound Cpd-E | 0.020 g |
| Compound Cpd-F | 0.040 g |
| Compound Cpd-K | 5.0 mg |
| High boiling point organic solvent Oil-1 | 0.020 g |
| High boiling point organic solvent Oil-2 | 0.020 g |

Twelfth layer (intermediate layer):

| | |
|---|---|
| Gelatin | 0.50 g |
| Additive M-1 | 0.050 g |

Thirteenth layer (yellow filter layer):

| | |
|---|---|
| Yellow colloidal silver | 0.080 g, based on Ag |
| Gelatin | 1.00 g |
| Color mixing inhibitor Cpd-A | 0.10 g |
| High boiling point organic solvent Oil-1 | 0.10 g |
| Microcrystalline solid dispersion of Dye E-2 | 0.050 g |

Fourteenth layer (intermediate layer):

| | |
|---|---|
| Gelatin | 0.50 g |

Fifteenth layer (low-speed blue-sensitive emulsion layer):

| | |
|---|---|
| Emulsion J | 0.20 g, based on Ag |
| Emulsion K | 0.30 g, based on Ag |
| Gelatin | 0.80 g |
| Coupler C-5 | 0.20 g |
| Coupler C-6 | 0.10 g |
| Coupler C-10 | 0.20 g |

Sixteenth layer (medium-speed blue-sensitive emulsion layer):

| | |
|---|---|
| Emulsion L | 0.30 g, based on Ag |
| Emulsion M | 0.30 g, based on Ag |
| Gelatin | 0.90 g |
| Coupler C-5 | 0.10 g |
| Coupler C-6 | 0.10 g |
| Coupler C-10 | 0.60 g |

Seventeenth layer (high-speed blue-sensitive emulsion layer):

| | |
|---|---|
| Emulsion N | 0.20 g, based on Ag |
| Emulsion O | 0.20 g, based on Ag |
| Gelatin | 1.20 g |
| Coupler C-5 | 0.10 g |
| Coupler C-6 | 0.10 g |
| Coupler C-10 | 0.60 g |
| High boiling point organic solvent Oil-2 | 0.10 g |

Eighteenth layer (first protective layer):

| | |
|---|---|
| Gelatin | 0.70 g |
| Ultraviolet absorbent U-1 | 0.20 g |
| Ultraviolet absorbent U-2 | 0.050 g |
| Ultraviolet absorbent U-5 | 0.030 g |
| Formaldehyde scavenger Cpd-H | 0.40 g |
| Dye D-1 | 0.15 g |
| Dye D-2 | 0.050 g |
| Dye D-3 | 0.10 g |

Nineteenth layer (second protective layer):

| | |
|---|---|
| Colloidal silver | 0.10 mg, based on Ag |
| Fine-grain silver iodobromide emulsion (having an average grain size of 0.06 μm and an iodide content of 1 mole %) | 0.10 g, based on Ag |
| Gelatin | 0.40 g |

Twentieth layer (third protective layer):

| | |
|---|---|
| Gelatin | 0.40 g |
| Polymethylmethacrylate (average particle size: 1.5 μm) | 0.10 g |
| Methylmethacrylate/acrylic acid (4/6) copolymer (average particle size: 1.5 μm) | 0.10 g |
| Silicone oil | 0.030 g |
| Surfactant W-1 | 3.0 mg |
| Surfactant W-2 | 0.030 g |

In addition to the above-described ingredients, additives F-1 to F-8 were added to all the emulsion layers. Further, a gelatin hardener H-1 and surfactants W-3, W-4, W-5 and W-6 as coating aids and emulsifying agents were added to every layer.

Furthermore, phenol, 1,2-benzisothiazoline-3-one, 2-phenoxyethanol, phenetyl alcohol and butyl p-benzoate were added as antiseptics and antimolds.

The silver iodobromide emulsions applied to Sample No. 101 are as follows:

TABLE 1-3

| Emulsion Name | Characteristics of Grains | Sphere corresponding average grain size (μm) | Variation coefficient (%) | AgI content (%) |
|---|---|---|---|---|
| A | monodisperse tetradeca-hedral grains | 0.28 | 16 | 4.0 |
| B | monodisperse cubic grains having high internal sensitivity but low surface sensitivity | 0.30 | 10 | 4.0 |
| C | monodisperse cubic grains | 0.38 | 10 | 5.0 |
| D | monodisperse tabular grains (average aspect ratio: 3.0) | 0.68 | 8 | 2.0 |
| E | monodisperse cubic grains | 0.20 | 17 | 4.0 |
| F | monodisperse tetradeca-hedral grains | 0.25 | 16 | 4.0 |
| G | monodisperse cubic grains having high internal sensitivity but low surface sensitivity | 0.40 | 11 | 4.0 |
| H | monodisperse cubic grains | 0.50 | 9 | 3.5 |
| I | monodisperse tabular grains (average aspect ratio: 5.0) | 0.80 | 10 | 2.0 |
| J | monodisperse cubic grains | 0.30 | 18 | 4.0 |
| K | monodisperse tetradeca-hedral grains | 0.45 | 17 | 4.0 |
| L | monodisperse tabular grains (average aspect ratio: 5.0) | 0.55 | 10 | 2.0 |
| M | monodisperse tabular grains (average aspect ratio: 8.0) | 0.70 | 13 | 2.0 |
| N | monodisperse tabular grains (average aspect ratio: 6.0) | 1.00 | 10 | 1.5 |
| O | monodisperse tabular grains (average aspect ratio: 9.0) | 1.20 | 15 | 1.5 |

TABLE 2

Spectral Sensitization of Emulsions A to I

| Emulsion Name | Sensitizing Dyes added | Amount (g) added per mole of Silver Halide |
|---|---|---|
| A | S - 2 | 0.025 |
| | S - 3 | 0.25 |
| | S - 8 | 0.010 |
| B | S - 1 | 0.010 |
| | S - 3 | 0.25 |
| | S - 8 | 0.010 |
| C | S - 1 | 0.010 |
| | S - 2 | 0.010 |
| | S - 3 | 0.25 |
| | S - 8 | 0.010 |
| D | S - 2 | 0.010 |
| | S - 3 | 0.10 |
| | S - 8 | 0.010 |
| E | S - 4 | 0.50 |
| | S - 5 | 0.10 |
| F | S - 4 | 0.30 |
| | S - 5 | 0.10 |
| G | S - 4 | 0.25 |
| | S - 5 | 0.08 |
| | S - 9 | 0.05 |
| H | S - 4 | 0.20 |
| | S - 5 | 0.060 |
| | S - 9 | 0.050 |
| I | S - 4 | 0.30 |
| | S - 5 | 0.070 |
| | S - 9 | 0.10 |

TABLE 3
Spectral Sensitization of Emulsions J to O
| Emulsion Name | Sensitizing Dyes added | Amount (g) added per mole of Silver Halide |
|---|---|---|
| J | S - 6 | 0.050 |
|   | S - 7 | 0.20 |
| K | S - 6 | 0.05 |
|   | S - 7 | 0.20 |
| L | S - 6 | 0.060 |
|   | S - 7 | 0.22 |
| M | S - 6 | 0.050 |
|   | S - 7 | 0.17 |
| N | S - 6 | 0.040 |
|   | S - 7 | 0.15 |
| O | S - 6 | 0.060 |
|   | S - 7 | 0.22 |
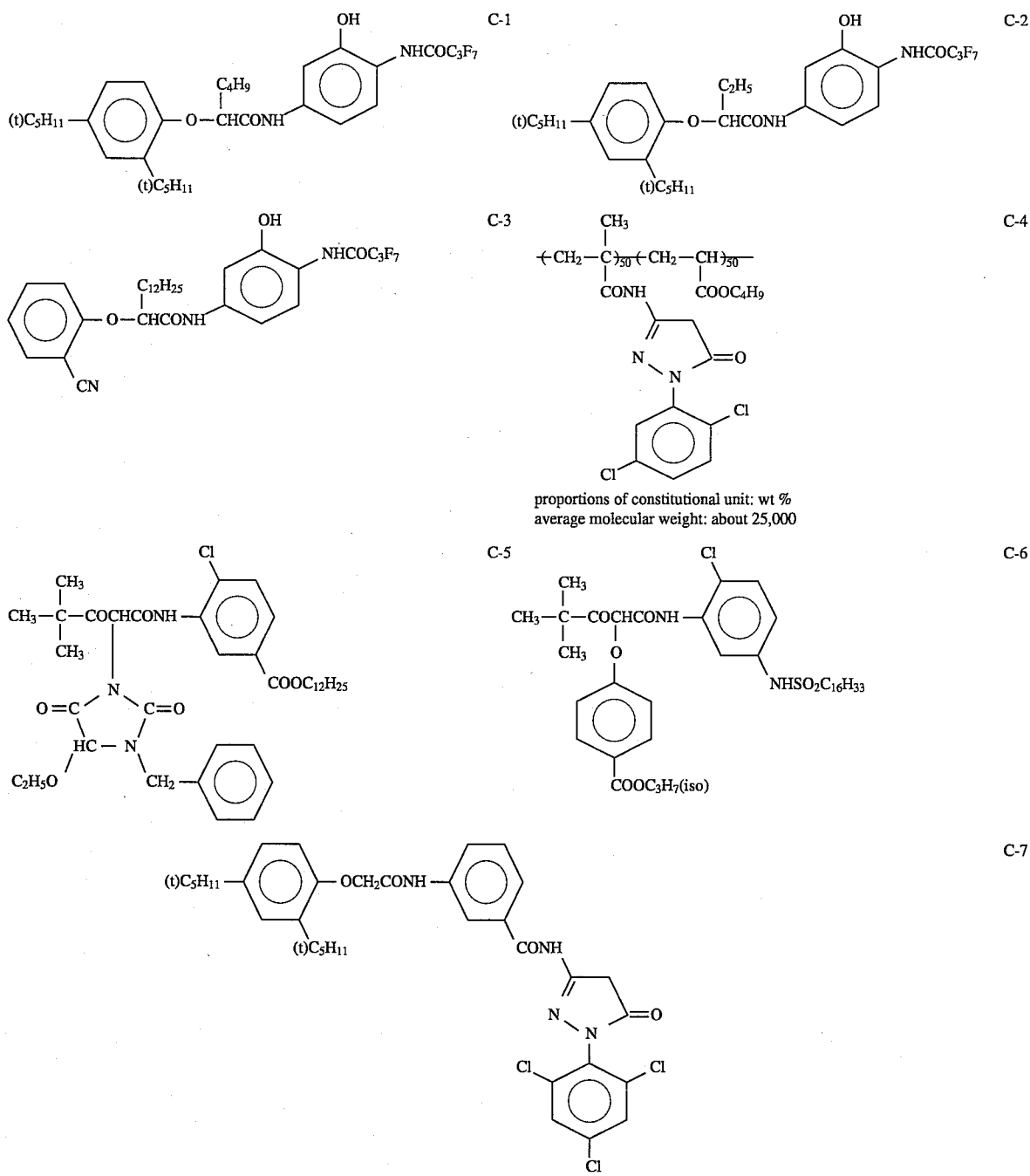

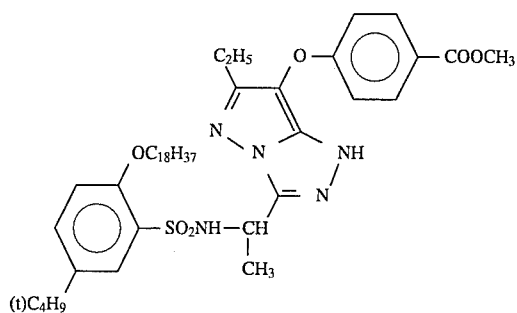
C-8
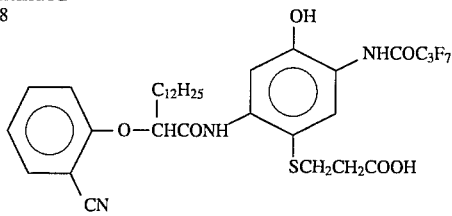
C-9
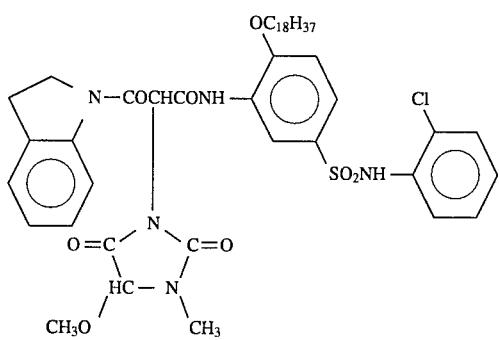
C-10
Dibutyl phthalate    Oil-1
Tricresyl phosphate    Oil-2
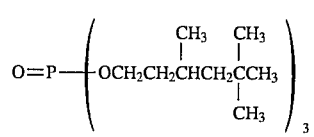
Oil-3
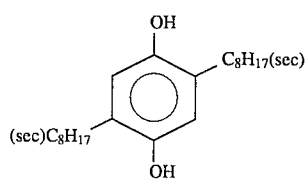
Cpd-A
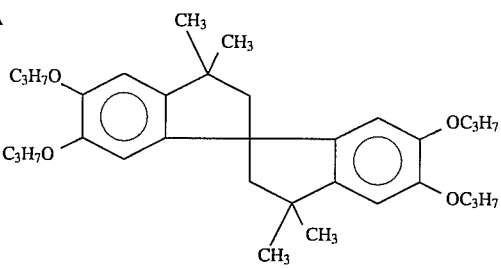
Cpd-B
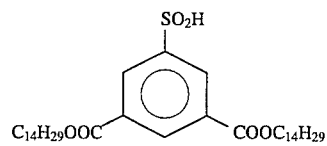
Cpd-C
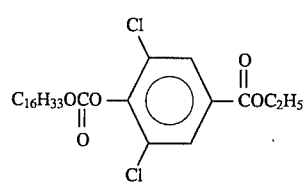
Cpd-D
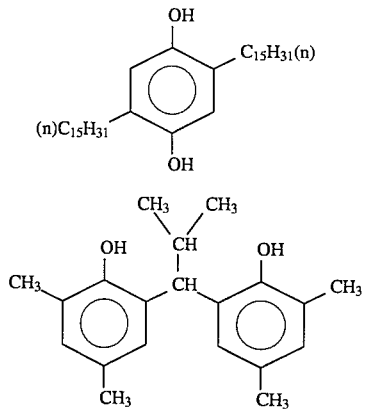
Cpd-E
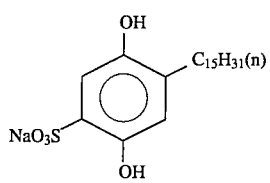
Cpd-F
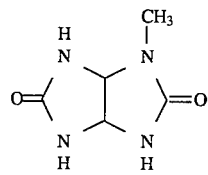
Cpd-H
Cpd-I -continued
Cpd-J
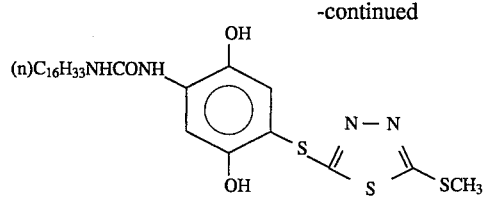
Cpd-K
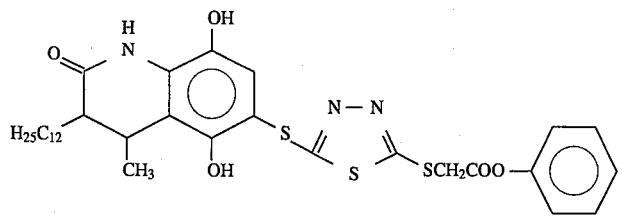
U-1
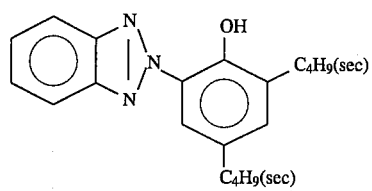
U-2
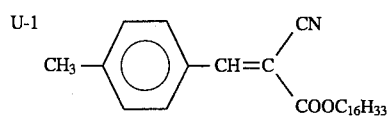
U-3
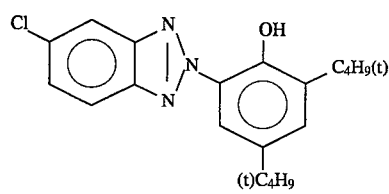
U-4
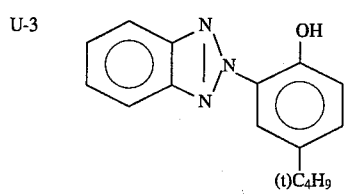
U-5
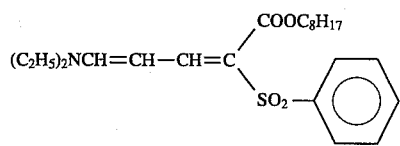
S-1
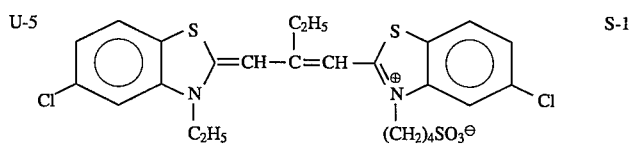
S-2
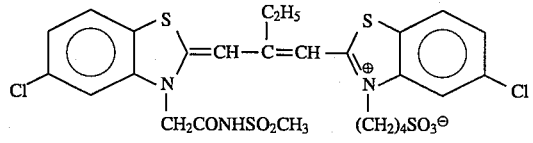
S-3
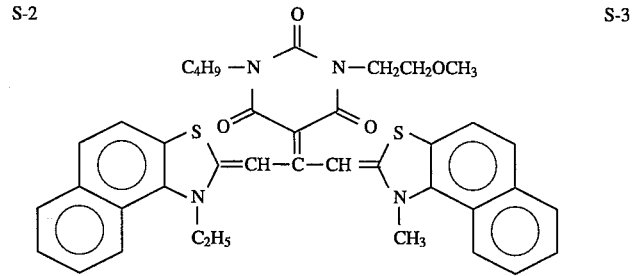
S-4
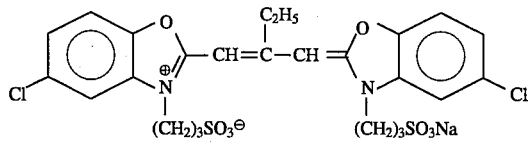
S-5
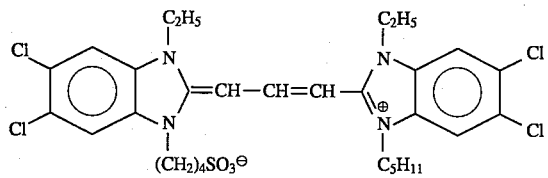
S-6
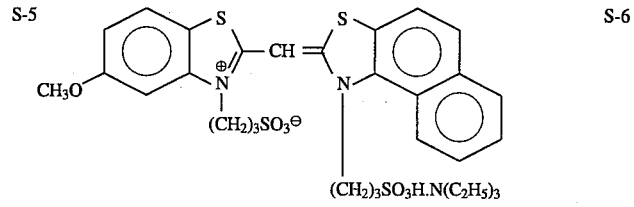

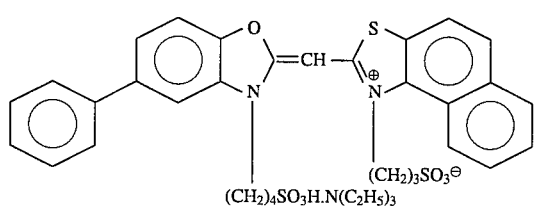
S-7
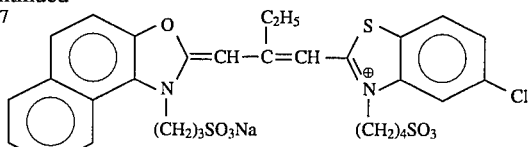
S-8
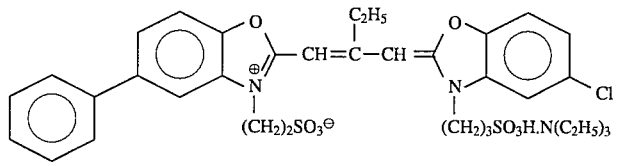
S-9
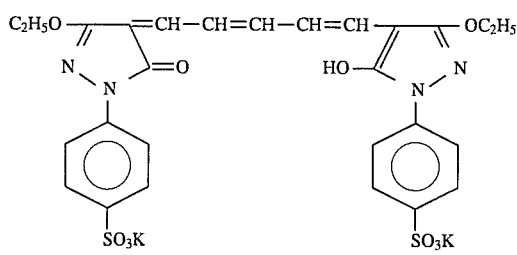
D-1
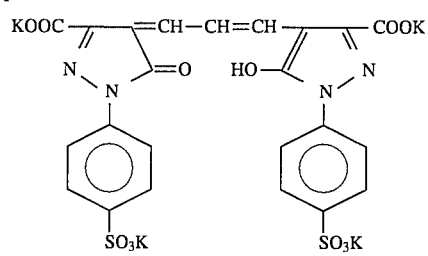
D-2
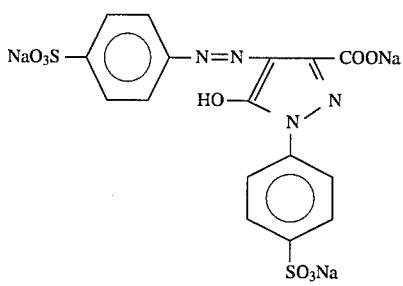
D-3
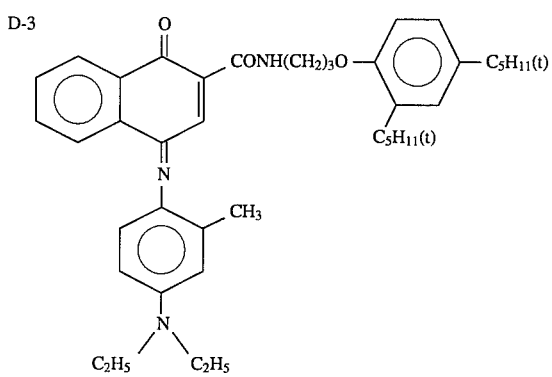
D-4
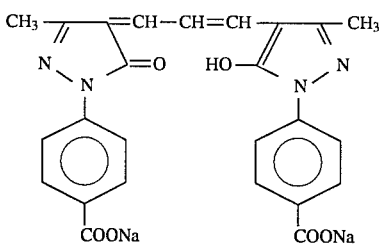
D-5
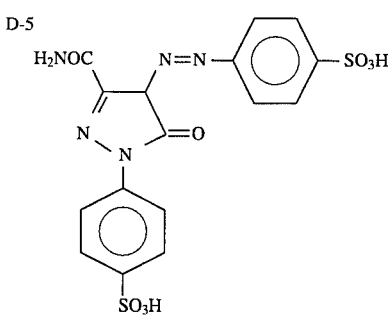
D-6
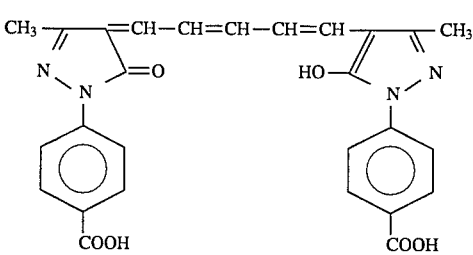
E-1
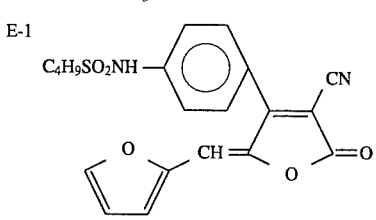
E-2

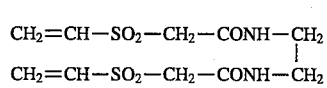
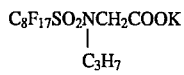
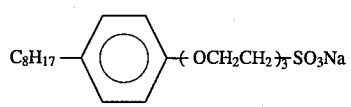
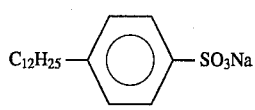
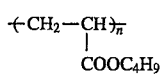
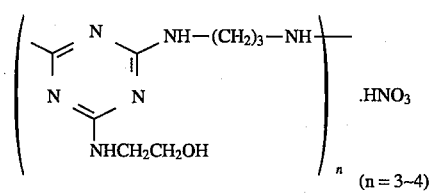
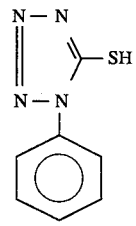
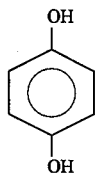
-continued
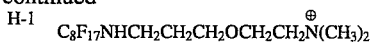  H-1   W-1
  W-2   W-3
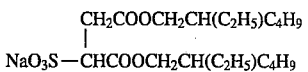  W-4   W-5
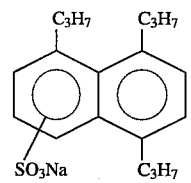  W-6   P-1
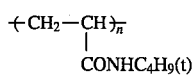  M-1   F-1
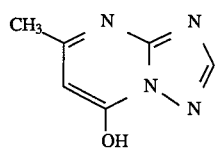  F-2   F-3
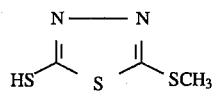  F-4   F-5
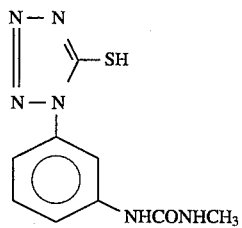  F-6   F-7
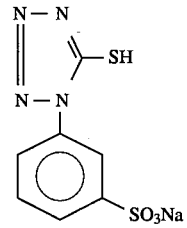  F-8
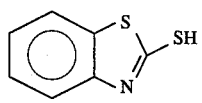
Comparative Compound A
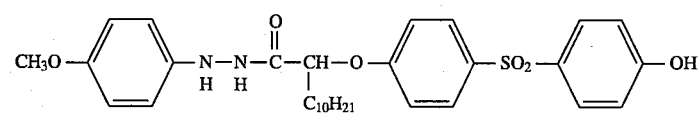
(Compound described in EP-A2-0338785)

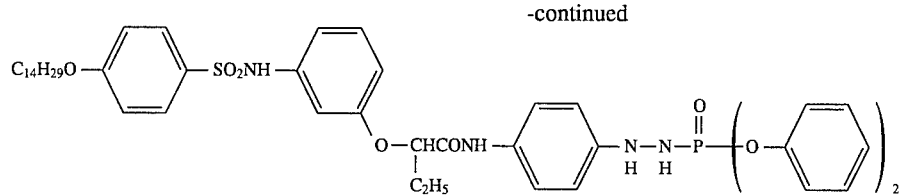

Comparative Compound B (Compound described in JP-A-03-164735)

Preparation of Sample Nos. 102 to 116

Sample Nos. 102 to 116 were prepared in the same manner as Sample No. 101, except that the color mixing inhibitor Cpd-A used in the eighth layer and the thirteenth layer of Sample No. 101 was replaced by equimolar amounts of Comparative Compound A, Comparative Compound B and the present compounds as set forth in Table 4, respectively.

Each of the thus prepared Sample Nos. 101 to 116 was cut into strips. One strip of each sample was subjected to wedge exposure through a red filter, and examined for minimum density of the cyan color-forming layer. The extent of color mixing caused in the red-sensitive layer by the green-sensitive layer was evaluated by the minimum density examined. Another strip of each sample was subjected to wedge exposure through a green filter, and examined for minimum density of the magenta color-forming layer, thereby evaluating the extent of color mixing caused in the green-sensitive layer by the blue-sensitive layer.

Still another strip of each sample was stored for 1 week under the condition of 45° C.-80% RH, then exposed to white light through a wedge, and compared with that of the other strip of each Sample which was stored at 25° C., thereby evaluating the keeping quality of each sample. The photographic processing adopted in these examinations is described below. The results obtained are shown in Table 4.

| Processing Step | Time | Temperature |
| --- | --- | --- |
| First development | 6 minutes | 38° C. |
| Washing | 2 minutes | 38° C. |
| Reversal | 2 minutes | 38° C. |
| Color development | 6 minutes | 38° C. |
| Prebleach | 2 minutes | 38° C. |
| Bleach | 6 minutes | 38° C. |
| Fixation | 4 minutes | 38° C. |
| Washing | 4 minutes | 38° C. |
| Final rinsing | 1 minute | 25° C. |

The composition of each processing solution was as follows:

[First Developer]

| | |
| --- | --- |
| Pentasodium nitrilo-N,N,N-trimethylenephosphonate | 1.5 g |
| Pentasodium diethylenetriaminepentaacetate | 2.0 g |
| Sodium sulfite | 30 g |
| Potassium hydroquinonemonosulfonate | 20 g |
| Potassium carbonate | 15 g |
| Sodium hydrogen carbonate | 12 g |
| 1-Phenyl-4-methyl-4-hydroxymethyl-3-pyrazolidone | 1.5 g |
| Potassium bromide | 2.5 g |
| Potassium thiocyanate | 1.2 g |
| Potassium iodide | 2.0 mg |
| Diethylene glycol | 13 g |
| Water to make | 1,000 ml |
| pH | 9.60 |

The pH was adjusted with sulfuric acid or potassium hydroxide.

[Reversing Bath]

| | |
| --- | --- |
| Pentasodium nitrilo-N,N,N-trimethylenephosphonate | 3.0 g |
| Stannous chloride dihydrate | 1.0 g |
| p-Aminophenol | 0.1 g |
| Sodium hydroxide | 8 g |
| Glacial acetic acid | 15 ml |
| Water to make | 1,000 ml |
| pH | 6.00 |

The pH was adjusted with acetic acid or sodium hydroxide.

[Color Developer]

| | |
| --- | --- |
| Pentasodium nitrilo-N,N,N-trimethylenephosphonate | 2.0 g |
| Sodium sulfite | 7.0 g |
| Sodium phosphate dodecahydrate | 36 g |
| Potassium bromide | 1.0 g |
| Potassium iodide | 90 mg |
| Sodium hydroxide | 3.0 g |
| Citrazinic acid | 1.5 g |
| N-Ethyl-N-(β-methanesulfonamidoethyl)-3-methyl-4-aminoaniline · 3/2 sulfate · monohydrate | 11 g |
| 3,6-Dithiaoctane-1,8-diol | 1.0 g |
| Water to make | 1,000 ml |
| pH | 11.80 |

The pH was adjusted with sulfuric acid or potassium hydroxide.

[Prebleach Bath]

| | |
| --- | --- |
| Disodium ethylenediaminetetraacetate dihydrate | 8.0 g |
| Sodium sulfite | 6.0 g |
| 1-Thioglycerol | 0.4 g |
| Formaldehyde-sodium bisulfite adduct | 30 g |
| Water to make | 1,000 ml |
| pH | 6.20 |

The pH was adjusted with acetic acid or sodium hydroxide.

[Bleaching Bath]

| | |
| --- | --- |
| Disodium ethylenediaminetetraacetate dihydrate | 2.0 g |
| Ammonium ethylenediaminetetraacetatoferrate(III) dihydrate | 120 g |
| Potassium bromide | 100 g |
| Ammonium nitrate | 10 g |
| Water to make | 1,000 ml |
| pH | 5.70 |

The pH was adjusted with nitric acid or sodium hydroxide.

| [Fixer] | |
|---|---|
| Ammonium thiosulfate | 80 g |
| Sodium sulfite | 5.0 g |
| Sodium bisulfite | 5.0 g |
| Water to make | 1,000 ml |
| pH | 6.60 |

The pH was adjusted with acetic acid or aqueous ammonia.

| [Final Rinsing Bath] | |
|---|---|
| 1,2-Benzoisothiazoline-3-one | 0.02 g |
| Polyoxyethylene-p-monononylphenylether (average polymerization degree: 10) | 0.3 g |
| Polymaleic acid (average molecular weight: 2,000) | 0.1 g |
| Water to make | 1,000 ml |
| pH | 7.0 | replaced by the present compound (1), (8) and (13) respectively. These samples A, B and C were exposed and development-processed in the same manners as in Example 1 of the patent gazette cited above. Therein, the results similar to in Example 1 of the present invention were obtained.

EXAMPLE 3

Preparation of Sample Nos. 104' to 116':

Sample Nos. 104' to 116' were prepared in the same manner as Sample No. 101 prepared in Example 1, except that the color mixing inhibitor Cpd-A used in the eighth layer and the thirteenth layer of Sample No. 101 was replaced by equimolar amounts of the present compounds as set forth in Table 5, respectively.

Each of the thus prepared Sample Nos. 104' to 116' as well as 'Sample Nos. 101 to 103 prepared in Example 1 was cut into strips. One strip of each sample was subjected to wedge exposure through a red filter, and examined for minimum density of the cyan color-forming layer. The extent of color mixing caused in the red-sensitive layer by the green-sensitive layer was evaluated by the minimum density examined. Another strip of each sample was subjected to

TABLE 4

| Sample No. | Compound in 8th layer and 13th layer | Color mixing caused in red-sensitive layer by green-sensitive layer | Color mixing caused in green-sensitive layer by blue-sensitive layer | Maximum density drop in green-sensitive layer after one-week storage under 45° C.–80% |
|---|---|---|---|---|
| 101 (comparison) | Cpd-A | 0.25 | 0.13 | 0.30 |
| 102 (comparison) | Comparative Compound A | 0.20 | 0.11 | 0.31 |
| 103 (comparison) | Comparative Compound B | 0.11 | 0.10 | 0.24 |
| 104 (invention) | (2) | 0.11 | 0.06 | 0.16 |
| 105 (invention) | (17) | 0.10 | 0.06 | 0.15 |
| 106 (invention) | (15) | 0.10 | 0.05 | 0.16 |
| 107 (invention) | (9) | 0.09 | 0.06 | 0.15 |
| 108 (invention) | (6) | 0.09 | 0.05 | 0.14 |
| 109 (invention) | (8) | 0.06 | 0.04 | 0.10 |
| 110 (invention) | (18) | 0.06 | 0.04 | 0.09 |
| 111 (invention) | (1) | 0.05 | 0.03 | 0.10 |
| 112 (invention) | (19) | 0.05 | 0.04 | 0.11 |
| 113 (invention) | (7) | 0.05 | 0.04 | 0.10 |
| 114 (invention) | (12) | 0.04 | 0.04 | 0.10 |
| 115 (invention) | (3) | 0.04 | 0.03 | 0.09 |
| 116 (invention) | (13) | 0.04 | 0.03 | 0.08 |

As can be seen from Table 4, Sample Nos. 104 to 116 in which were used the color mixing inhibitors of the present invention had excellent ability to inhibit the interlayer color mixing, and suffered a small change by storage in the developed color density of a magenta color-forming layer. Therefore, they had a slight change in gradation. Of the samples according to the present invention, Sample Nos. 109 to 116 have proved to be more excellent in ability to inhibit the color mixing and in keeping quality.

EXAMPLE 2

Samples A, B and C were prepared in the same manner as Sample No. 101 of Example 1 in JP-A-06-236014, except that the Compound Cpd-1 in the 6th and 10th layers was wedge exposure through a green filter, and examined for minimum density of the magenta color-forming layer, thereby evaluating the extent of color mixing caused in the green-sensitive layer by the blue-sensitive layer.

Still another strip of each'sample was stored for 1 week under the condition of 45° C.-80% RH, then exposed to white light through a wedge, and compared with that of the other strip of each Sample which was stored at 25° C., thereby evaluating the keeping quality of each sample. The photographic processing adopted in these examinations is the same as in Example 1. The results obtained are shown in Table 5.

TABLE 5

| Sample No. | Compound in 8th layer and 13th layer | Color mixing caused in red-sensitive layer by green-sensitive layer | Color mixing caused in green-sensitive layer by blue-sensitive layer | Maximum density drop in green-sensitive layer after one-week storage under 45° C.–80% |
|---|---|---|---|---|
| 101 (comparison) | Cpd-A | 0.25 | 0.13 | 0.30 |
| 102 (comparison) | Comparative Compound A | 0.20 | 0.11 | 0.31 |
| 103 (comparison) | Comparative Compound B | 0.11 | 0.10 | 0.24 |
| 104' (invention) | (13)' | 0.10 | 0.07 | 0.16 |
| 105' (invention) | (18)' | 0.09 | 0.06 | 0.15 |
| 106' (invention) | (12)' | 0.09 | 0.06 | 0.14 |
| 107' (invention) | (9)' | 0.08 | 0.05 | 0.13 |
| 108' (invention) | (8)' | 0.08 | 0.05 | 0.13 |
| 109' (invention) | (11)' | 0.06 | 0.05 | 0.10 |
| 110' (invention) | (15)' | 0.05 | 0.04 | 0.10 |
| 111' (invention) | (23)' | 0.05 | 0.03 | 0.10 |
| 112' (invention) | (5)' | 0.05 | 0.04 | 0.09 |
| 113' (invention) | (10)' | 0.04 | 0.03 | 0.09 |
| 114' (invention) | (22)' | 0.03 | 0.03 | 0.09 |
| 115' (invention) | (7)' | 0.03 | 0.03 | 0.08 |
| 116' (invention) | (17)' | 0.03 | 0.02 | 0.07 |

As can be seen from Table 5, Sample Nos. 104' to 116' in which were used the color mixing inhibitors of the present invention had excellent ability to inhibit the interlayer color mixing, and suffered a small change by storage in the developed color density of a magenta color-forming layer. Therefore, they had a slight change in gradation. Of the samples according to the present invention, Sample Nos. 109' to 116' have proved to be more excellent in ability to inhibit the color mixing and in keeping quality.

EXAMPLE 4

Samples A', B' and C' were prepared in the same manner as Sample No. 101 of Example 1 in JP-A-06-236014, except that the Compound Cpd-1 in the 6th and 10th layers was replaced by the present compound (1)', (8)' and (13)' respectively. These samples A', B' and C' were exposed and development-processed in the same manners as in Example 1 of the patent gazette cited above. Therein, the results similar to in Example 3 of the present invention were obtained.

EXAMPLE 5

1) Support

The support used in this example was prepared in the following manner: 100 Parts by weight of a polyethylene-2,6-naphthalate polymer and 2 parts of a ultraviolet absorbent, Tinuvin P.326 (trade name, a product of Ciba-Geigy) were dried, and then fused at 300° C. Thereafter, the fused matter was extruded from a T-die, and elongated by a factor of 3.3 in the longitudinal direction at 140° C., followed by elongation by a factor of 3.3 in the horizontal direction at 130° C. Further, the thus elongated film underwent 6-second thermal setting at 250° C. to give a PEN film having a thickness of 90 μm. Additionally, appropriate amounts of blue, magenta and yellow dyes (Dyes I-1, I-4, I-6, I-24, I-27 and II-5 described in Kokai Giho No. 94-6023) were added to the polymer in advance of the extrusion. Furthermore, the PEN film was wound onto a stainless roll having a diameter of 20 cm, and thereon was conferred 48-hour heat history at 110° C. to render the film hard to curl.

2) Formation of Subbing Layer

Both surfaces of the support prepared above were subjected to a corona discharge treatment, a UV discharge treatment, and further a glow discharge treatment. The thus treated support was coated with a 10 cc/m$^2$ of subbing solution wherein were contained 0.1 g/m$^2$ of gelatin, 0.01 g/m$^2$ of sodium α-sulfodi-2-ethylhexylsuccinate, 0.04 g/m$^2$ of salicylic acid, 0.2 g/m$^2$ of p-chlorophenol, 0.012 g/m$^2$ of $(CH_2=CHSO_2CH_2CH_2NHCO)_2CH_2$ and 0.02 g/m$^2$ of a polyamideepichlorohydrin polycondensate (by means of a bar coater) on the side which had been the high temperature side in the aforesaid elongation step. The thus coated solution was dried at 115° C. for 6 minutes (the temperature of the rollers and conveying apparatus installed in the drying zone was set at 115° C.).

3) Formation of Backing Layer

After forming the subbing layer on one side of the support, the other side of the support was provided with a backing layer constituted of antistatic, magnetic recording and slipping layers which had the following compositions respectively.

3-1) Formation of Antistatic Layer:

The back surface of the support was coated with 0.2 g/m$^2$ of a dispersion of finely divided tin oxide-antimony oxide complex powder having an average grain diameter of 0.005 μm and a specific resistance of 5 Ω.cm (secondarily aggregated grain size: about 0.08 μm), 0.05 g/m$^2$ of gelatin, 0.02 g/m$^2$ of $(CH_2=CHSO_2CH_2CH_2NHCO)_2CH_2$, 0.005 g/m$^2$ of polyoxyethylene(polymerization degree: 10)-p-nonylphenol and resorcinol.

3-2) Formation of Magnetic Recording Layer 0.06 g/m$^2$ of cobalt-γ-iron oxide (having the specific surface area of 43 m$^2$/g, the major axis of 0 14 μm, the minor axis of 0.03 μm, the saturation magnetization of 89 emu/g, the $Fe^{+2}/Fe^{+3}$ ratio of 6/94 and the grain surface treated with aluminum oxide and silicon oxide in the amount corresponding to 2 wt. % of the iron oxide) covered with 3-poly(polymerization degree: 15)oxyethylenepropyloxytrimethoxysilane (15 wt. %) was coated by means of a bar coater together with 1.2 g/m$^2$ of diacetyl cellulose (the dispersion of the iron oxide thereinto was carried out with an open kneader and a sand mill), 0.3 g/m$^2$ of $C_2H_5C(CH_2OCONHC_6H_3(CH_3)NCO)_3$ as a hardener and a mixture of acetone, methyl ethyl ketone and cyclohexanone as a solvent, thereby forming a magnetic recording layer having a thickness of 1.2 μm. Additionally, 10 mg/m² of silica grains (0.3 μm) as a matting agent and 10 mg/m² of aluminum oxide (0.15 μm) coated with 3-poly(polymerization degree: 15)oxyethylenepropyloxytrimethoxysilane (15 wt. %) as an abrasive were also added thereto. The drying was carried out at 115° C. for 6 minutes (the temperature of the rollers and conveying apparatus installed in the drying zone was set at 115° C.). The gain in color density $D^B$ of the thus formed magnetic recording layer upon exposure to X-light (blue filter) was about 0.1. Further, the saturation magnetization of the magnetic recording layer was 4.2 emu/g, the coercive force thereof was $7.3 \times 10^4$ A/m, and the rectangular ratio was 65%.

3-3) Formation of Slipping Layer

Diacetyl cellulose (25 mg/m²) and a mixture of $C_6H_3CH(OH)C_{10}H_{20}COOC_{40}H_{81}$ (Compound a, 6 mg/m²) with $C_{50}H_{101}O(CH_2CH_2O)_{16}H$ (Compound b, 9 mg/m²) were coated. Additionally, the mixture was prepared as follows: Compounds a and b are fused at 105° C. in a xylene/propylene monomethyl ether (1/1) mixture, poured and dispersed into propylene monomethyl ether (10 times the amount of the poured matter) having ordinary temperature, and further made into a dispersion (average particle size: 0.01 μm) in acetone. Further, silica grains (0.3 μm) as a matting agent and aluminum oxide (0.15 μm) coated with 3-poly(polymerization degree: 15)oxyethylene-propyloxytrimethoxysilane (15 wt. %) as an abrasive were added to the dispersion so that each of them might have a coverage rate of 15 mg/m². The coating was dried at 115° C. for 6 minutes (the temperature of the rollers and conveying apparatus installed in the drying zone was set at 115° C.). The thus formed slipping layer had a kinematic friction coefficient of 0.06 (5 mm φ stainless ball, 100 g of load, 6 cm/min. of speed) and a static friction coefficient of 0.07 (Clip method). With respect to the friction between the slipping layer and an emulsion layer described below, the kinematic friction coefficient was 0.12. That is, the slipping layer formed had excellent characteristics.

4) Formation of Photosensitive Layer

On the side opposed to the backing layer formed in the above-described manner, the same emulsions as used for preparing Sample No. 101 in Example 1 were coated over the support in the multilayer form to prepare Sample No. 201'. Similarly thereto, Sample No. 216' was prepared using the same emulsions as used for preparing Sample No. 116' in Example 3.

5) Evaluation

These samples were evaluated by the same methods as adopted in Example 3. Thus, it has been found that Sample No. 216' had distinct improvements in color turbidity, photodiscoloration and keeping quality, compared with Sample No. 201'.

EXAMPLE 6

Preparation of Sample Nos. 104" to 116":

Sample Nos. 104" to 116" were prepared in the same manner as Sample No. 101 in Example 1, except that the color mixing inhibitor Cpd-A used in the eighth layer and the thirteenth layer of Sample No. 101 was replaced by equimolar amounts of the present compounds as set forth in Table 6, respectively.

Each of the thus prepared Sample Nos.104" to 116" as well as Sample Nos. 101 to 103 obtained in Example 1 was cut into strips. One strip of each sample was subjected to wedge exposure through a red filter, and examined for minimum density of the cyan color-forming layer. The extent of color mixing caused in the red-sensitive layer by the green-sensitive layer was evaluated by the minimum density examined. Another strip of each sample was subjected to wedge exposure through a green filter, and examined for minimum density of the magenta color-forming layer, thereby evaluating the extent of color mixing caused in the green-sensitive layer by the blue-sensitive layer.

Still another strip of each sample was stored for 1 week under the condition of 45° C.-80% RH, then exposed to white light through a Wedge, and compared with that of the other strip of each Sample which was stored at 25° C., thereby evaluating the keeping quality of each sample. The photographic processing adopted in these examinations is the same as in Example 1. The results obtained are shown in Table 6.

TABLE 6

| Sample No. | Compound in 8th layer and 13th layer | Color mixing caused in red-sensitive layer by green-sensitive layer | Color mixing caused in green-sensitive layer by blue-sensitive layer | Maximum density drop in green-sensitive layer after one-week storage under 45° C.-80% |
|---|---|---|---|---|
| 101 (comparison) | Cpd-A | 0.25 | 0.13 | 0.30 |
| 102 (comparison) | Comparative Compound A | 0.20 | 0.11 | 0.31 |
| 103 (comparison) | Comparative Compound B | 0.11 | 0.10 | 0.24 |
| 104" (invention) | (22)" | 0.10 | 0.06 | 0.18 |
| 105" (invention) | (21)" | 0.10 | 0.06 | 0.17 |
| 106" (invention) | (17)" | 0.09 | 0.06 | 0.17 |
| 107" (invention) | (23)" | 0.09 | 0.05 | 0.16 |
| 108" (invention) | (5)" | 0.08 | 0.05 | 0.16 |
| 109" (invention) | (7)" | 0.06 | 0.05 | 0.12 |
| 110" (invention) | (14)" | 0.06 | 0.04 | 0.12 |
| 111" (invention) | (12)" | 0.05 | 0.04 | 0.10 |
| 112" (invention) | (13)" | 0.05 | 0.03 | 0.09 |
| 113" (invention) | (11)' | 0.04 | 0.04 | 0.09 |
| 114" (invention) | (15)" | 0.04 | 0.03 | 0.08 |
| 115" (invention) | (16)" | 0.04 | 0.03 | 0.08 |
| 116" (invention) | (1)" | 0.03 | 0.03 | 0.07 |

As can be seen from Table 6, Sample Nos. 104" to 116" in which were used the color mixing inhibitors of the present invention had excellent ability to inhibit the interlayer color mixing, and suffered a small change by storage in the developed color density of a magenta color-forming layer. Therefore, they had a slight change in gradation. Of the samples according to the present invention, Sample Nos. 109" to 116" using the present compounds in which both R"$^1$ and R"$^2$ were aryl groups have proved to be more excellent in ability to inhibit the color mixing and in keeping quality.

EXAMPLE 7

Samples A", B" and C" were prepared in the same manner as Sample No. 101 of Example 1 in JP-A-06-236014, except that the Compound Cpd-1 in the 6th and 10th layers was replaced by the present compound (1)", (8)" and (13)" respectively. These samples A", B" and C" were exposed and development-processed in the same manners as n Example 1 of the patent gazette cited above. Therein, the results similar to in Example 6 of the present invention were obtained.

EXAMPLE 8

Preparation of 1) a support, and formation of 2) a subbing layer and 3) a backing layer [constituted of 3-1) an antistatic layer, 3-2) a magnetic recording layer and 3-3) a slipping layer] were carried out in the same manners as in Example 5, respectively.

Further, 4) a photosensitive layer was formed on the subbing layer (or on the side opposed to the backing layer). In forming the photosensitive layer, the same emulsions as used for preparing Sample No. 101 in Example 1 were coated over the support in the multilayer form to prepare Sample No. 201". Similarly thereto, Sample No. 220" was prepared using the same emulsions as used for preparing Sample No. 116" in Example 6.

These samples were evaluated by the same methods as adopted in Example 6. Thus, it has been found that Sample No. 220" had distinct improvements in color turbidity, photodiscoloration and keeping quality, compared with Sample No. 201".

While the invention has been described in detail and with reference to specific embodiments thereof, it will be apparent to one skilled in the art that various changes and modifications can be made therein without departing from the spirit and scope thereof.

What is claimed is:

1. A silver halide color photosensitive material having on a support at least one photosensitive silver halide emulsion layer, said material containing at least one nondiffusible compound represented by the following formula (I), (I-1) or (I-2):

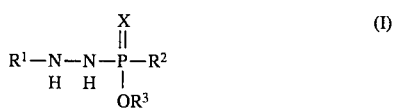

wherein R$^1$ represents an aryl group or a heterocyclic group, R$^2$ represents an alkyl group, a cycloalkyl group, an alkoxy group or an aryloxy group, R$^3$ represents an alkyl group, a cycloalkyl group, an aryl group or a heterocyclic group and X represents an oxygen atom or a sulfur atom; provided that R$^3$ does not represent a phenyl group when R$^2$ represents a phenoxy group:

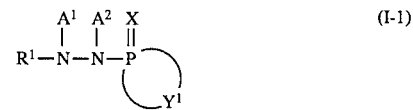

wherein R$^1$ represents an aryl group or a heterocyclic group; A$^1$ and A$^2$ each represents a hydrogen atom or a hydrolyzable group; X represent an oxygen atom or a sulfur atom; and Y$^1$ represents atoms completing a phosphorus atom-containing heterocyclic ring:

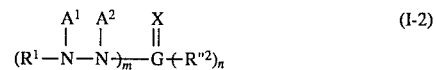

wherein R$^1$ represents an aryl group or a heterocyclic group; R"$^2$ represents an alkyl group, a cycloalkyl group, an aryl group, a heterocyclic group, an alkoxy group or an aryloxy group; A$^1$ and A$^2$ each represents a hydrogen atom or a hydrolyzable group; G represents a carbon atom or a phosphorus atom; X represents an oxygen atom or a sulfur atom; when G represents a carbon atom, m is 2 and n is 0; when G represents a phosphorus atom, m is 2 and n is 1, or m is 3 and n is 0; and when m is 2 or more, two or three R$^1$N(A$^1$)N(A$^2$)— groups may be the same or different.

2. A silver halide color photosensitive material as described in claim 1, wherein said compound represented by formula (I-1) is a compound represented by the following formula ( II-1 )

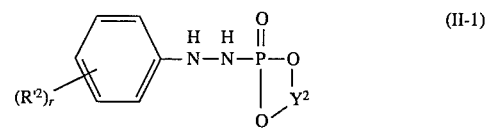

wherein R'$^2$ represents a substituent group, r is an integer of from 0 to 5, and Y$^2$ represents atoms completing a 5- to 10-membered heterocyclic ring which comprises a —O—(PO)—O— linkage and carbon atoms.

3. A silver halide color photosensitive material as described in claim 1, wherein said compound represented by the formula (I-2) is a compound represented by the following formula (II-2):

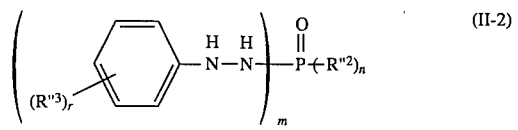

wherein R"$^2$ represents an alkyl group, a cycloalkyl group, an aryl group, a heterocyclic group, an alkoxy group or an aryloxy group; m is 2 or 3; n is 1 when m is 2, or n is 0 when m is 3; r is an integer of from 0 to 5; R"$^3$ represents a substituent group, and when r is not less than 2, a plurality of R"$^3$ groups may be the same or different.

4. A silver halide color photosensitive material as described in claim 3, wherein the compound represented by the formula (II-2) is a compound represented by the following formula (III-2):

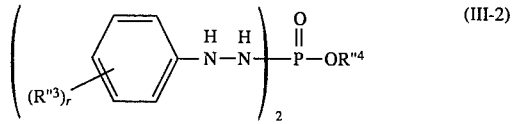

wherein R"$^4$ represents an alkyl group or an aryl group; r is an integer of from 0 to 5; and R"$^3$ represents a substituent group, and when r is not less than 2, a plurality of R"$^3$ groups may be the same or different.

5. A silver halide color photosensitive material as described in claim 1, wherein at least one of $R^1$, $R^2$ and $R^3$ in the formula (I), at least one of $R^1$ and $Y^1$ in the formula (I-1), and at least one of $R^1$ and $R^{"2}$ in the formula (I-2) has a ballast group which contains at least 8 carbon atoms.

6. A silver halide color photosensitive material as described in claim 1, wherein said nondiffusible compound represented by the formula (I), (I-1) or (I-2) is used in a total amount of 0.001 to 0.8 g/m² in the photosensitive material.

7. A silver halide color photosensitive material as described in claim 1, wherein said nondiffusible compound represented by the formula (I), (I-1) or (I-2) is incorporated in the interlayer arranged between two light-sensitive emulsion layers.

8. A silver halide color photographic material having on a support at least one photosensitive silver halide emulsion layer, said material containing at least one nondiffusible compound represented by formula (I)

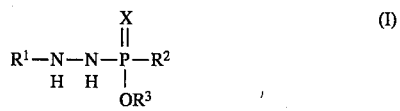

wherein $R^1$ represents an aryl group or a heterocyclic group, $R^2$ represents an alkyl group, a cycloalkyl group, an alkoxy group or an aryloxy group, $R^3$ represents an alkyl group, a cycloalkyl group, an aryl group or a heterocyclic group and X represents an oxygen atom or sulfur atom; provided that $R^3$ does not represent a phenyl group when $R^2$ represents a phenoxy group.

9. The silver halide color photographic material as described in claim 8, wherein at least one of $R^1$, $R^2$ and $R^3$ is a ballast group (i) containing at least 8 carbon atoms and (ii) having no adverse affect on photographic properties.

10. The silver halide color photographic material as described in claim 8, wherein $R^1$ represents an aryl group or a heterocyclic group, $R^2$ represents a substituted or unsubstituted alkoxy group, and represents a substituted or unsubstituted alkoxy group.

11. The silver halide color photographic material as described in claim 8, wherein $R^1$ represents an aryl group or a heterocyclic group, $R^2$ represents a substituted or unsubstituted alkoxy group, $R^3$ represents a substituted or unsubstituted alkoxy group, and at least one of $R^1$, $R^2$ and $R^3$ is a ballast group (i) containing at least 8 carbon atoms and (ii) having no adverse affect on photographic properties.

12. The silver halide color photosensitive material as described in claim 1, wherein $R^1$ or $R^3$ represent a substituted or unsubstituted aryl group having 6–30 carbon atoms, or a substituted or unsubstituted heterocyclic group having 3–8 members which contain as a hetero atom a member selected from the group consisting of oxygen, nitrogen, sulfur and combinations thereof.

13. The silver halide color photosensitive material as claimed in claim 1, wherein a substituent for $R^1$, $R^2$, or $R^3$ are selected from group consisting of an alkyl group, an aryl group, an acylamino group, an alkoxy group, an aryloxy group, an alkylthio group, an arylthio group, an acyl group, a sulfonyl group, a sulfonylamino group, a cyano group, an alkoxycarbonyl group, an aryloxycarbonyl group, a carbamoyl group, a sulfamoyl group, a carboxyl group, a halogen atom and a hydroxyl group.

14. The silver halide color photosensitive material as described in claim 2, wherein $R^{'2}$ is selected from the group consisting of an alkyl group, an aryl group, an acylamino group, an alkoxy group, an aryloxy group, an alkylthio group, an arylthio group, an acyl group, a sulfonyl group, a sulfonylamino group, a cyano group, an alkoxycarbonyl group, an aryloxycarbonyl group, a carbamoyl group, a sulfamoyl group, a carboxyl group, a halogen atom and a hydroxyl group.

15. The silver halide color photosensitive material as described in claim 3, wherein $R^{"3}$ is selected from the group consisting of an alkyl group, an aryl group, an acylamino group, an alkoxy group, an aryloxy group, an alkylthio group, an arylthio group, an acyl group, a sulfonyl group, a sulfonylamino group, a cyano group, an alkoxycarbonyl group, an aryloxycarbonyl group, a carbamoyl group, a sulfamoyl group, a carboxyl group, a halogen atom and a hydroxyl group.

16. The silver halide color photosensitive material as described in claim 1, wherein $R^2$ or $R^3$ represent a substituted or unsubstituted alkyl group containing to 60 carbon atoms or a substituted or unsubstituted cycloalkyl group containing 3 to 60 carbon atoms.

17. The silver halide color photosensitive material as described in claim 1, wherein said compound represented by formula (I) is selected from the group consisting of:

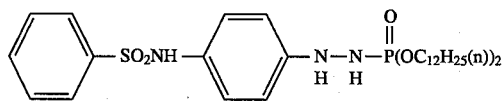

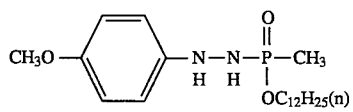

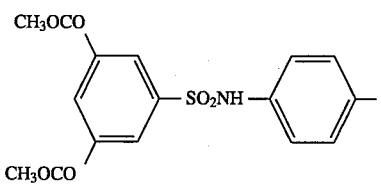

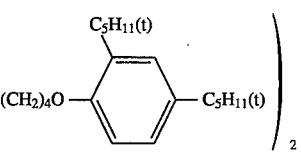

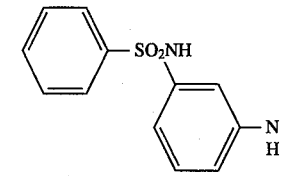

-continued
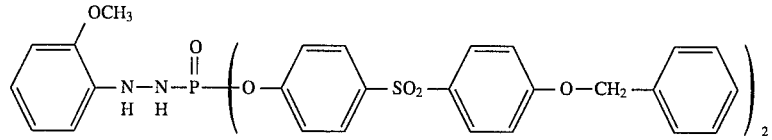 (5)
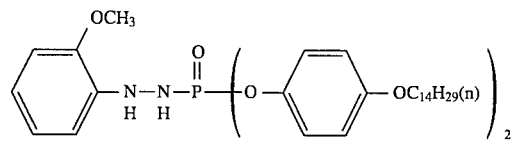 (6)
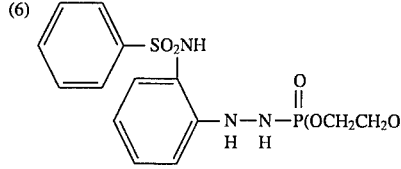 (7)
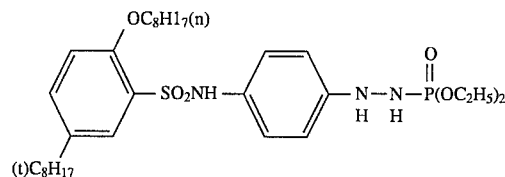 (8)
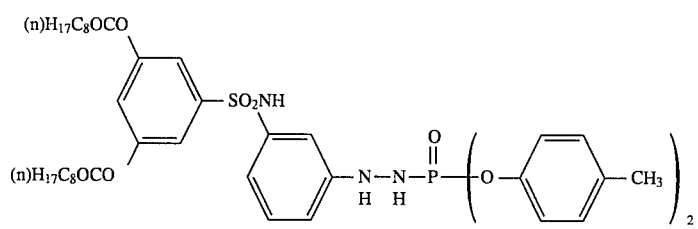 (9)
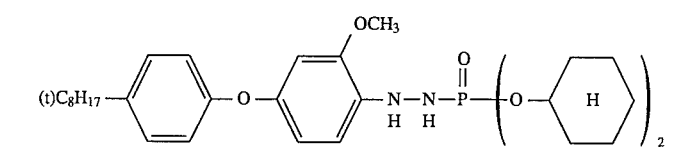 (10)
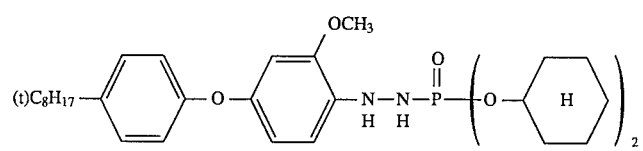 (11)
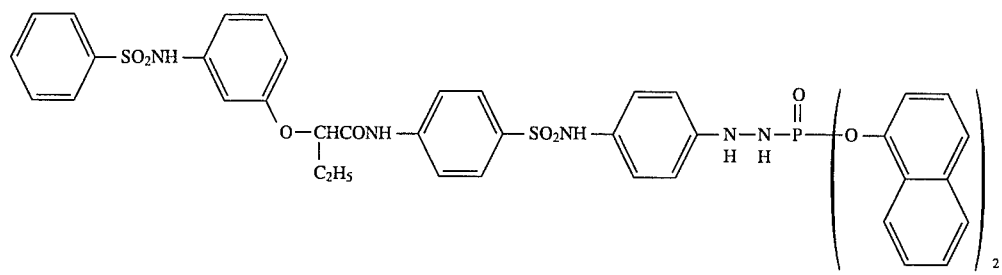 (12)
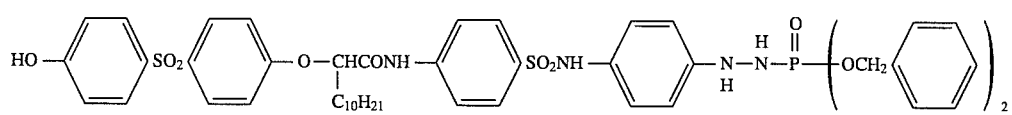 (13)
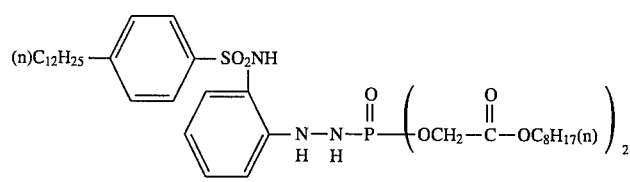 (14)
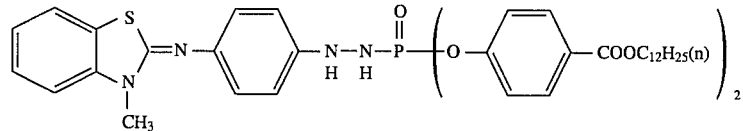 (15)
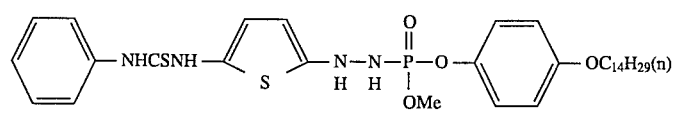

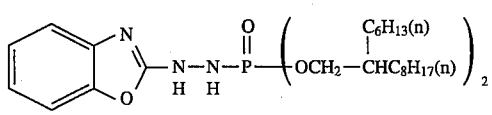 (16)
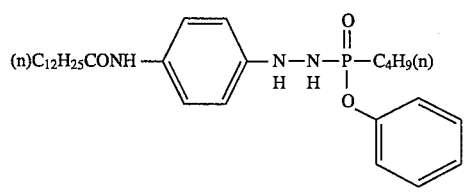 (17)

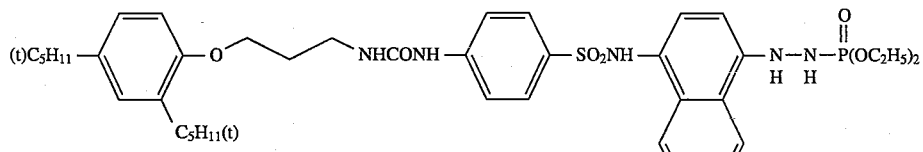 (18)

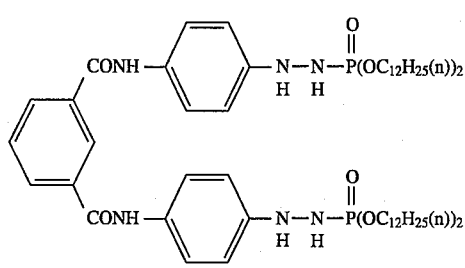 (19) and
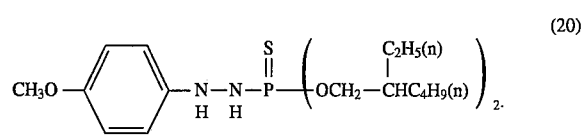 (20)

18. The silver halide color photosensitive material as described in claim 2, wherein $R'^2$ is selected from the group consisting of an acylamino group a sulfonamido group, an alkoxy group, an alkyl group, and a chlorine atom.

19. The silver halide color photosensitive material as described in claim 1, wherein the compound represented by formula (I-1) is selected from the group consisting of:

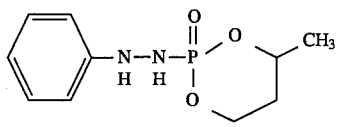 (1)'
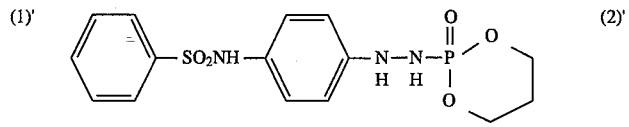 (2)'

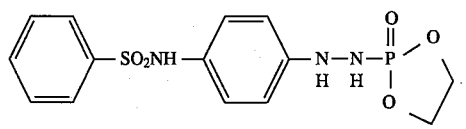 (3)'
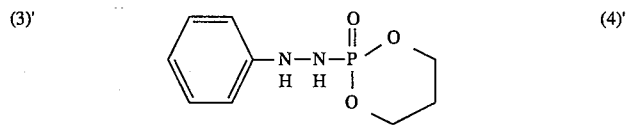 (4)'

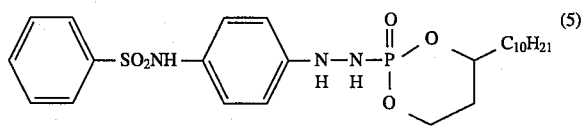 (5)'
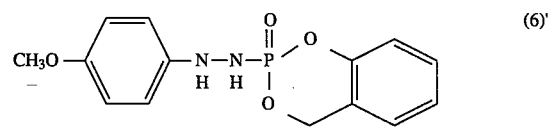 (6)'

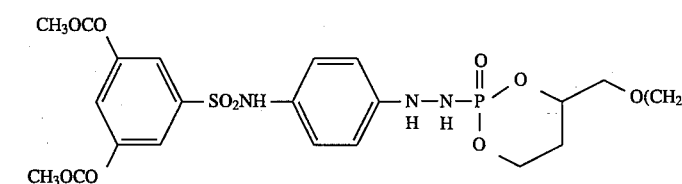 (7)'

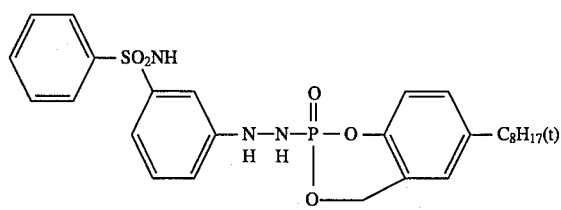 (8)'
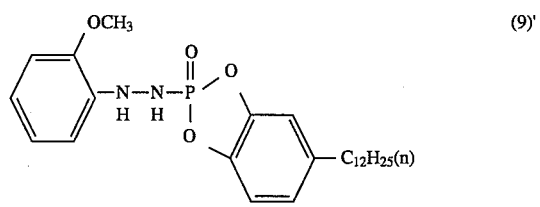 (9)'

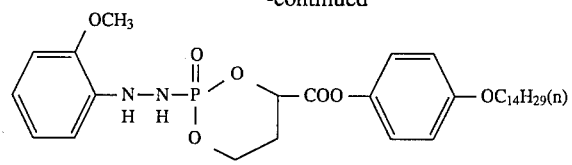
(10)'
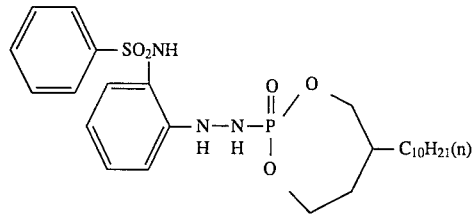
(11)'
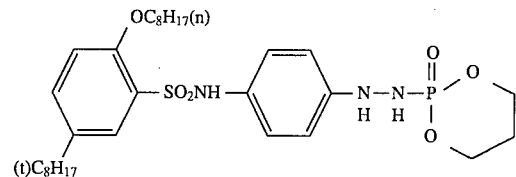
(12)'
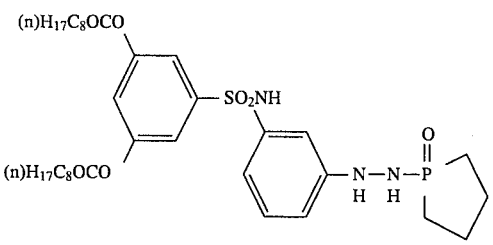
(13)'
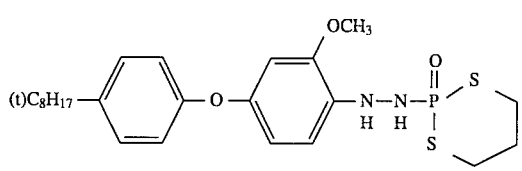
(14)'
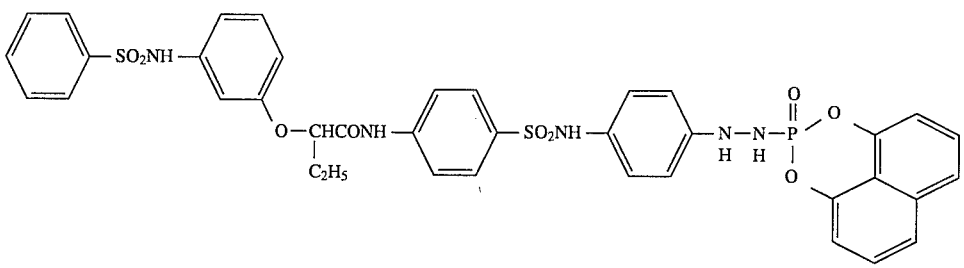
(15)'
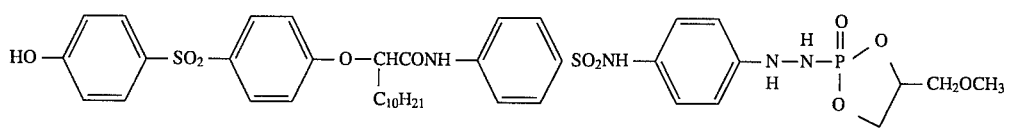
(16)'
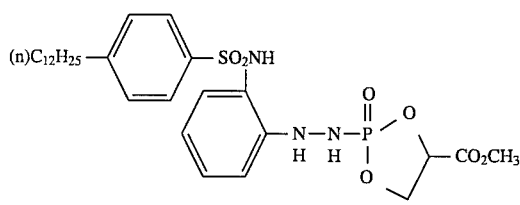
(17)'
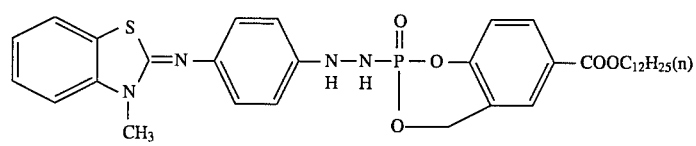
(18)'
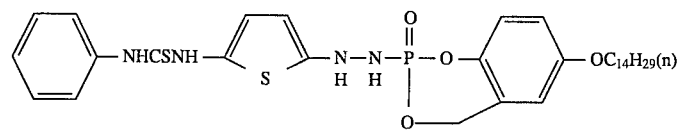
(19)'
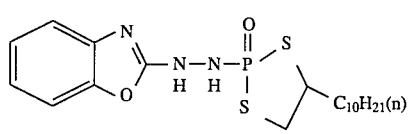
(20)'
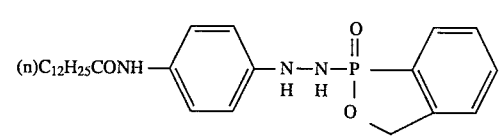
(21)'

20. The silver halide color photosensitive material a described in claim 3, wherein $R^{"3}$ is selected from the group consisting of an acylamino group, a sulfonamido group, an alkoxy group, an alkyl group and a chlorine atom.

21. The silver halide color photosensitive material as described in claim 1, wherein the compound represented by formula (I-2) is selected from the group consisting of:

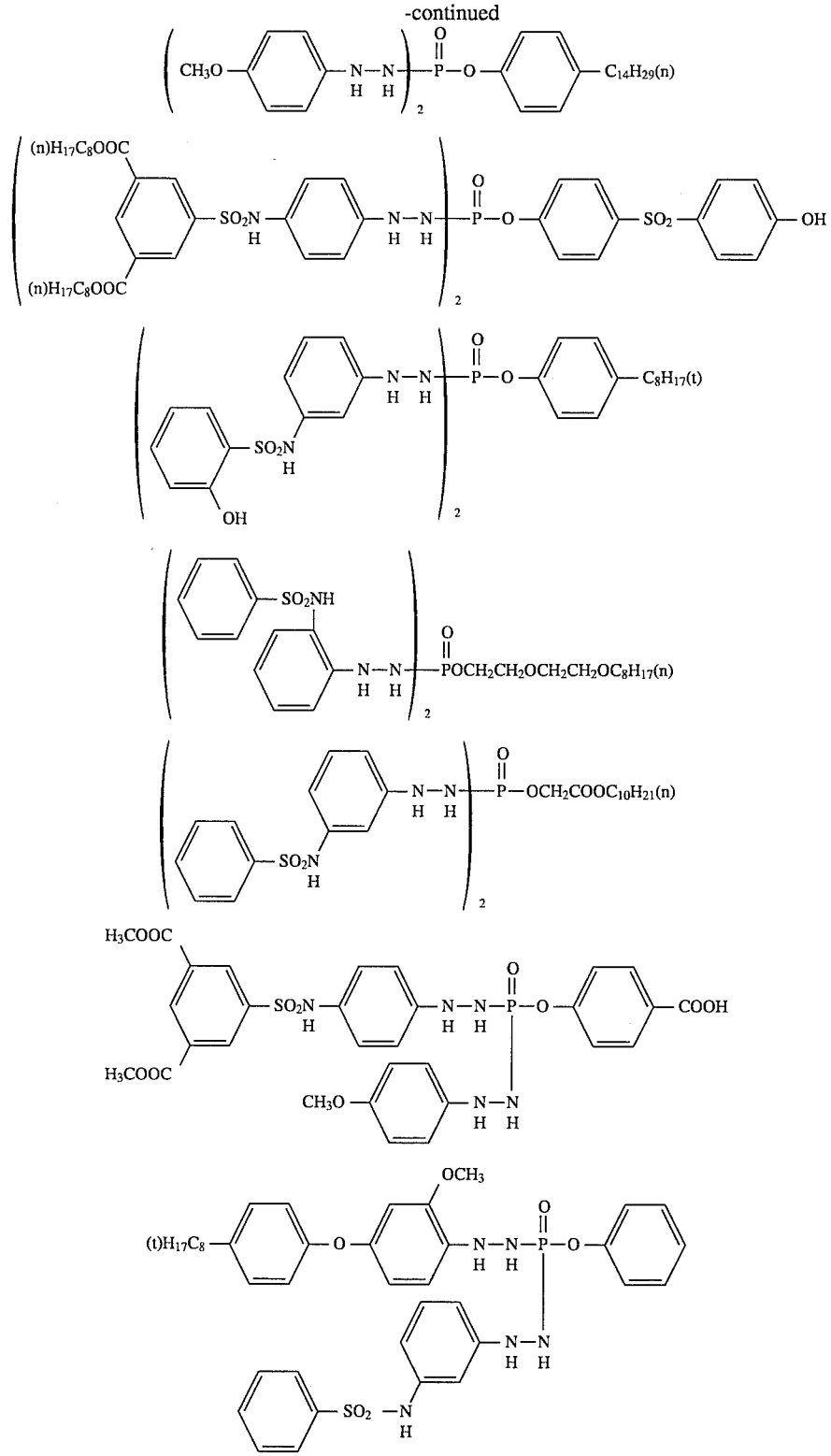

-continued
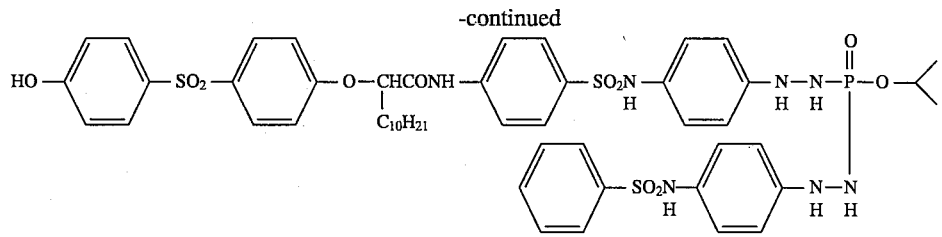   17")
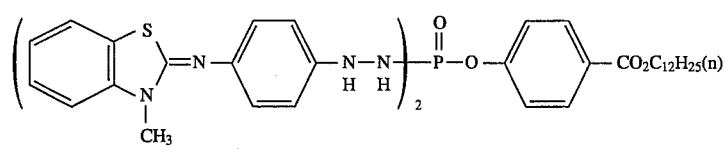   18")
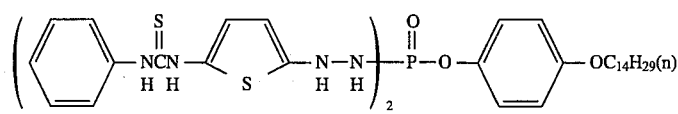   19")
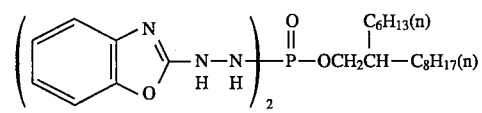   20")
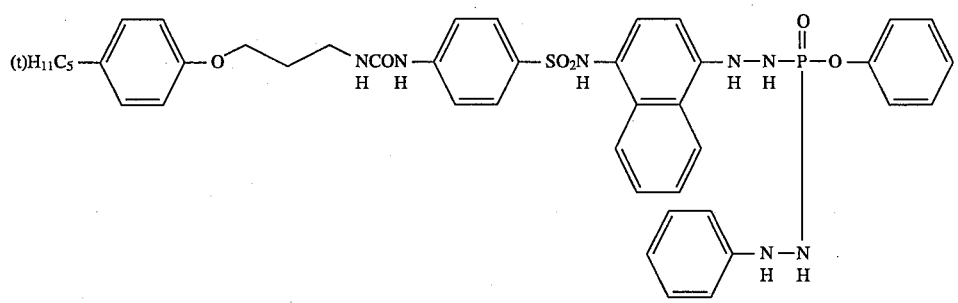   21")
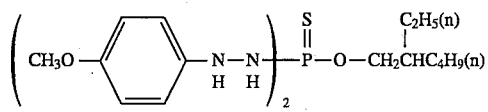   22")
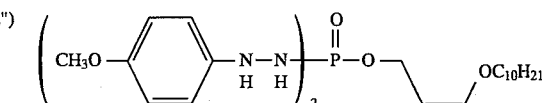   23")
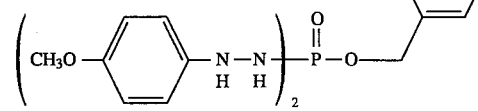   24")
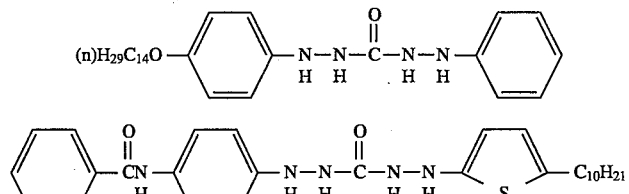   25")
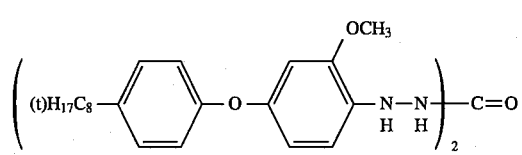   26")
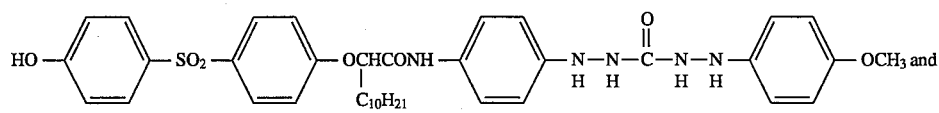   27")

-continued
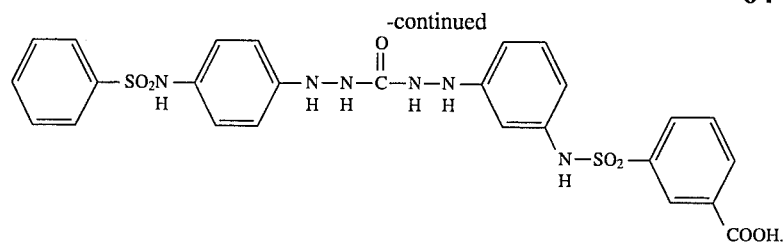
22. A method for preventing color stain and color contamination in a color photographic material which comprises processing the silver halide color photosensitive material according to claim 1 in a color development process using an aromatic primary amine color developing agent.
* * * * *